(12) United States Patent
Dogra et al.

(10) Patent No.: US 8,870,770 B2
(45) Date of Patent: *Oct. 28, 2014

(54) LOW-COST DEVICE FOR C-SCAN ACOUSTIC WAVE IMAGING

(71) Applicant: University of Rochester, Rochester, NY (US)

(72) Inventors: Vikram S. Dogra, Pittsford, NY (US); Navalgund A. H. K. Rao, Rochester, NY (US)

(73) Assignee: University of Rochester, Rochester, NY (US)

( * ) Notice: Subject to any disclaimer, the term of this patent is extended or adjusted under 35 U.S.C. 154(b) by 141 days.

This patent is subject to a terminal disclaimer.

(21) Appl. No.: 13/712,117

(22) Filed: Dec. 12, 2012

(65) Prior Publication Data

US 2013/0102875 A1 Apr. 25, 2013

Related U.S. Application Data

(63) Continuation of application No. 12/505,264, filed on Jul. 17, 2009, now Pat. No. 8,353,833.

(60) Provisional application No. 61/081,946, filed on Jul. 18, 2008.

(51) Int. Cl.
*A61B 8/00* (2006.01)
*A61B 5/00* (2006.01)
*G01S 7/52* (2006.01)

(52) U.S. Cl.
CPC ............. *A61B 5/0095* (2013.01); *A61B 5/4337* (2013.01); *A61B 5/4312* (2013.01); *A61B 5/0091* (2013.01); *A61B 5/4381* (2013.01); *A61B 5/418* (2013.01); *G01S 7/52061* (2013.01); *A61B 5/4571* (2013.01); *A61B 8/4416* (2013.01); *A61B 5/0059* (2013.01); *A61B 5/415* (2013.01)
USPC .......................................... 600/437; 600/476

(58) Field of Classification Search
USPC ......................................... 600/437, 443, 476
See application file for complete search history.

(56) References Cited

U.S. PATENT DOCUMENTS 3,982,223 A 9/1976 Green
4,624,143 A 11/1986 Green
(Continued)

FOREIGN PATENT DOCUMENTS

CN 101015464 A 8/2007
CN 100353910 C 12/2007
(Continued)

OTHER PUBLICATIONS

Kaufmann, et al., "Aspects of human fetoplacental vasculogenesis and angiogenesis: II. Changes during normal pregnancy," Placenta, 2004, pp. 114-126, vol. 25, Elsevier, Maryland Heights, MO, USA. Ltd., Maryland Heights, MO, USA.

(Continued)

*Primary Examiner* — Jonathan Cwern
(74) *Attorney, Agent, or Firm* — Riverside Law LLP

(57) ABSTRACT

The prostate gland or other region of interest is stimulated with either a light source or an ultrasound source, resulting in photoacoustic or ultrasound acoustic waves which are focused by an acoustic lens and captured by a specific 1- or 2D sensor array and subsequently displayed as a C-scan on a computer screen. The amplitude of the waves generated by the stimulation is proportional to the optical absorption of the tissue element at that spatial location. Variability in tissue absorption results in C-scan image contrast.

57 Claims, 19 Drawing Sheets

(56) References Cited

U.S. PATENT DOCUMENTS

| | | | |
|---|---|---|---|
| 4,913,142 A | 4/1990 | Kittrell et al. | |
| 5,184,601 A | 2/1993 | Putman | |
| 5,413,197 A | 5/1995 | Baer et al. | |
| 5,433,204 A | 7/1995 | Olson | |
| 5,483,958 A | 1/1996 | Merberg et al. | |
| 5,533,508 A | 7/1996 | Doiron | |
| 5,534,997 A | 7/1996 | Schrader et al. | |
| 5,537,499 A | 7/1996 | Brekke | |
| 5,907,395 A | 5/1999 | Schulz et al. | |
| 6,102,857 A | 8/2000 | Kruger | |
| 6,130,071 A | 10/2000 | Alitalo et al. | |
| 6,238,348 B1 | 5/2001 | Crowley et al. | |
| 6,377,514 B1 | 4/2002 | Linnenbrink et al. | |
| 6,384,951 B1 | 5/2002 | Basiji et al. | |
| 6,572,609 B1 | 6/2003 | Farr et al. | |
| 6,593,101 B2 | 7/2003 | Richards-Kortum et al. | |
| 6,615,063 B1 | 9/2003 | Ntziachristos et al. | |
| 7,037,325 B2 | 5/2006 | Svanberg et al. | |
| 7,399,278 B1 | 7/2008 | Ross | |
| 7,606,394 B2 | 10/2009 | Mirtsching | |
| 7,613,330 B2 | 11/2009 | Mirtsching et al. | |
| 8,277,241 B2 | 10/2012 | Horchler et al. | |
| 2001/0047136 A1 | 11/2001 | Domanik et al. | |
| 2001/0051766 A1 | 12/2001 | Gazdzinski | |
| 2002/0035361 A1 | 3/2002 | Houser et al. | |
| 2002/0045811 A1 | 4/2002 | Kittrell et al. | |
| 2002/0118870 A1 | 8/2002 | Youvan et al. | |
| 2002/0123023 A1 | 9/2002 | Sicurelli et al. | |
| 2002/0138073 A1 | 9/2002 | Intintoli et al. | |
| 2002/0141625 A1 | 10/2002 | Nelson | |
| 2003/0009205 A1 | 1/2003 | Biel | |
| 2003/0013973 A1 | 1/2003 | Georgakoudi et al. | |
| 2003/0018324 A1 | 1/2003 | Davenport et al. | |
| 2003/0099166 A1 | 5/2003 | Chan et al. | |
| 2003/0199860 A1 | 10/2003 | Loeb et al. | |
| 2004/0044287 A1 | 3/2004 | Lin et al. | |
| 2004/0095855 A1 | 5/2004 | Minase | |
| 2004/0155049 A1 | 8/2004 | Float et al. | |
| 2004/0172163 A1 | 9/2004 | Varis | |
| 2004/0243123 A1 | 12/2004 | Grasso et al. | |
| 2005/0182392 A1 | 8/2005 | Brucker et al. | |
| 2005/0187471 A1 | 8/2005 | Kanayama et al. | |
| 2005/0203353 A1 | 9/2005 | Ma et al. | |
| 2007/0010805 A1 | 1/2007 | Fedewa et al. | |
| 2007/0012777 A1 | 1/2007 | Tsikos et al. | |
| 2007/0088346 A1 | 4/2007 | Mirizzi et al. | |
| 2007/0233185 A1 | 10/2007 | Anderson et al. | |
| 2007/0299341 A1 | 12/2007 | Wang et al. | |
| 2008/0123083 A1 | 5/2008 | Wang et al. | |
| 2008/0183077 A1 | 7/2008 | Moreau-Gobard et al. | |
| 2008/0192897 A1 | 8/2008 | Piorek et al. | |
| 2009/0023168 A1 | 1/2009 | Park et al. | |
| 2009/0024043 A1 | 1/2009 | MacLeod et al. | |
| 2009/0252392 A1 | 10/2009 | Panarace | |

FOREIGN PATENT DOCUMENTS

| | | | |
|---|---|---|---|
| DE | 2521659 A1 | 12/1976 | |
| DE | 4240769 | 6/1994 | |
| EP | 0323920 | 7/1989 | |
| EP | 0521797 | 1/1993 | |
| EP | 0533543 | 3/1993 | |
| GB | 2157842 | 10/2008 | |
| WO | 9321842 A1 | 11/1993 | |
| WO | 96/20638 A1 | 7/1996 | |
| WO | 96/20683 | 7/1996 | |
| WO | 99/17668 A1 | 4/1999 | |
| WO | 99-22652 A1 | 5/1999 | |
| WO | 2004100761 A2 | 11/2004 | |

OTHER PUBLICATIONS

Demir, et al., "Classification of human placental stem villi: review of structural and functional aspects," Microscopy Research and Technique, 1997, pp. 29-41, vol. 38, Wiley, Hoboken, NJ, USA.

Kosanke, et al., "Branching patterns of human placental villous trees: perspectives of topological analysis," Placenta, 1993, pp. 591-604, vol. 14, Elsevier, Maryland Heights, MO, USA.

Kaufmann, et al., "Classification of human placental villi: I. Histology," Cell and Tissue Research, 1979, pp. 409-423, vol. 200, Springer, New York, NY, USA.

Kingdom, et al., "Development of the placental villous tree and its consequences for fetal growth," European Journal of Obstetrics & Gynecology and Reproductive Biology, 2000, pp. 35-43, vol. 92, Elsevier, Maryland Heights, MO, USA.

Charnock-Jones, et al., "Aspects of human fetoplacental vasculogenesis and angiogenesis: I. Molecular regulation," Placenta, 2004, pp. 103-113, vol. 25, Elsevier, Maryland Heights, MO, USA.

Mayhew, et al., "Aspects of human fetoplacental vasculogenesis and angiogenesis: III. Changes in complicated pregnancies," Placenta, 2004, pp. 127-139, vol. 25, Elsevier, Maryland Heights, MO, USA.

Demir, et al., "Fetal vasculogenesis and angiogenesis in human placental villi," Acta Anat, 1989, pp. 190-203, vol. 136, Karger AG, Basel, Switzerland.

Benirschke, "Basic Structure of the Villous Trees," Chapter 6 in The Pathology of the Placenta, 2002, pp. 50-115, Springer-Verlag, New York, USA.

Benirschke, "Angioarchitecture of Villi: Vascular Arrangment in Immature Villi," in The Pathology of the Placenta, 2002, pp. 140-146, Springer, New York, NY, USA.

Grether, et al., "Reliability of placental histology using archived specimens," Paediatric Perinatal Epidemiology, 1999, pp. 489-495, vol. 13, Wiley, Hoboken, NJ, USA.

Khong, et al., "Observer reliability in assessing placental maturity by histology," Journal of Clinical Pathology, 1995, pp. 420-423, vol. 48, BMJ, London, UK.

Khong, "Placental vascular development and neonatal outcome," Seminars in Neonatology, 2004, pp. 255-263, vol. 9, Elsevier, Maryland Heights, MO, USA.

Jaddoe, et al., "Hypotheses on the fetal origins of adult diseases: contributions of epidemiological studies," European Journal of Epidemiology, 2006, pp. 91-102, vol. 21, Springer, New York, NY, USA.

De Boo, et al., "The developmental origins of adult disease (Barker) hypothesis," Australian and New Zealand Journal of Obstetrics and Gynaecology, 2006, pp. 4-14, vol. 46, Wiley, Hoboken, NJ, USA.

Barker, et al., "The developmental origins of insulin resistance," Hormone Research, 2005, pp. 2-7, vol. 64, suppl 3, Karger AG, Basel, Switzerland.

Levitt, et al., "The foetal origins of the metabolic syndrome—a South African perspective," Cardiovascular Journal of South Africa, 2002, pp. 179-180, vol. 13, No. 4, Durbanville, South Africa.

Barker, "The fetal origins of type 2 diabetes mellitus," Annals of Internal Medicine, 1999, pp. 322-324, vol. 130, No. 4, pt. 1, Philadelphia, PA, USA.

Adair, et al., "Developmental determinants of blood pressure in adults," Annual Review of Nutrition, 2005, pp. 407-434, vol. 25, Palo Alto, CA, USA.

Levitt, et al., "Adult BMI and fat distribution but not height amplify the effect of low birthweight on insulin resistance and increased blood pressure in 20-year-old South Africans," Diabetologia, 2005, pp. 1118-1125, vol. 48, Springer, New York, NY, USA.

Levitt, et al., "An inverse relation between blood pressure and birth weight among 5 year old children from Soweto, South Africa," Journal of Epidemiology and Community Health, 1999, pp. 264-268. vol. 53, BMJ, London, UK.

Barker, et al., "The intrauterine and early postnatal origins of cardiovascular disease and chronic bronchitis," Journal of Epidemiology and Community Health, 1989, pp. 237-240, vol. 43, BMJ, London, UK.

Barker, et al., "The maternal and fetal origins of cardiovascular disease," Journal of Epidemiology and Community Health, 1992, pp. 8-11, vol. 46, BMJ, London, UK.

Tanis, et al., "Dutch women with a low birth weight have an increased risk of myocardial infarction later in life: a case control study," Reproductive Health, 2005, pp. 1-4, vol. 2, No. 1, Springer, New York, NY, USA.

(56) References Cited

OTHER PUBLICATIONS

Rich-Edwards, et al., "Longitudinal study of birth weight and adult body mass index in predicting risk of coronary heart disease and stroke in women," BMJ Online First, 2005, 300 p. 1115, BMJ, London, UK.

Lawlor, et al., "Birth weight is inversely associated with incident coronary heart disease and stroke among individuals born in the 1950s: findings from the Aberdeen Children of the 1950s prospective cohort study," Circulation, 2005, pp. 1414-1418, vol. 112, Lippincott Williams & Wilkins, Hagerstown, MD, USA.

Cooper, et al., "Review: developmental origins of osteoporotic fracture," Osteoporosis International, 2006, pp. 337-347, vol. 17, Springer, New York, NY, USA.

Gluckman, et al., "Life-long echoes—a critical analysis of the developmental origins of adult disease model," Biology of the Neonate, 2005, pp. 127-139, vol. 87, Karger AG, Basel, Switzerland.

Jasienska, et al., "High ponderal index at birth predicts high estradiol levels in adult women," American Journal of Human Biology, 2006, pp. 133-140, vol. 18, Wiley, Hoboken, NJ, USA.

Lagiou, et al., "Diet during pregnancy and levels of maternal pregnancy hormones in relation to the risk of breast cancer in the offspring," European Journal of Cancer Prevention, 2006, pp. 20-26, vol. 15, Lippincott Williams & Wilkins, Hagerstown, MD, USA.

Lagiou, et al., "Maternal height, pregnancy estriol and birth weight in reference to breast cancer risk in Boston and Shanghai," International Journal of Cancer, 2005, pp. 494-498, vol. 117, Wiley, Hoboken, NJ, USA.

Nilsen, et al., "Birth size and subsequent risk for prostate cancer: a prospective population-based study in Norway," International Journal of Cancer, 2005, pp. 1002-1004, vol. 113, Wiley, Hoboken, NJ, USA.

Asbury, et al., "Birthweight-discordance and differences in early parenting relate to monozygotic twin differences in behaviour problems and academic achievement at age 7," Developmental Science, 2006, pp. F22-F31, vol. 9, No. 2, Wiley, Hoboken, NJ, USA.

Bellingham-Young, et al., "Prematurity and adult minor illness," Neuroendocrinology Letters, 2004, pp. 117-126, vol. 25, suppl. 1, Society of Integrated Sciences.

Nilsson, et al., "Fetal growth restriction and schizophrenia: a Swedish twin study," Twin Research and Human Genetics, 2005, pp. 402-408, vol. 8, No. 4. Australian Academic Press, Bowen Hills, Australia.

Gunnell, et al., "The association of fetal and childhood growth with risk of schizophrenia. Cohort study of 720,000 Swedish men and women," Schizophrenia Research, 2005, pp. 315-322, vol. 79, Elsevier, Maryland Heights, MO, USA.

Willinger, et al., "Neurodevelopmental schizophrenia: obstetric complications, birth weight, premorbid social withdrawal and learning disabilities," Neuropsychobiology, 2001, pp. 163-169, vol. 43, Karger AG, Basel, Switzerland.

Talbert, "Uterine flow velocity waveform shape as an indicator of maternal and placental development failure mechanisms: a model-based synthesizing approach," Ultrasound in Obstetrics and Gynecology, 1995, pp. 261-271, vol. 6, Wiley, Hoboken, NJ, USA.

Naeye, "Disorders of the Placenta and Decidua," in Disorders of the Placenta, Fetus and Neonata, 1992, pp. 129-134, Mosby Year Book: Philadelphia, PA, USA.

Benirschke, "Placental Shape Aberrations," Chapter 13, in Pathology of the Human Placenta, 2002, pp. 452-472, Springer, New York, NY, USA.

Naeye, "Disorders of the Placenta and Decidua," in Disorders of the Placenta, Fetus and Neonata, 1992, pp. 129-130, Mosby Year Book: Philadelphia, PA, USA.

Benirschke, "Classification of Villous Maldevelopment," Chapter 15, in Pathology of the Human Placenta, 2002, pp. 437-460, Springer, New York, NY, USA.

Kaufmann, et al., "Cross-sectional features and three-dimensional structure of human placental villi," Placenta, 1987, pp. 235-247, vol. 8, Elsevier, Maryland Heights, MO, USA. Ltd., Maryland Heights, MO, USA.

Schweikhart, et al., "Morphology of placental villi after premature delivery and its clinical relevance," Archives of Gynecology, 1986, pp. 101-114, vol. 239, Springer, New York, NY, USA.

Larsen, et al., "Stereologic examination of placentas from mothers who smoke during pregnancy," American Journal of Obstetrics & Gynecology, 2002, pp. 531-537, vol. 186, Elsevier, Maryland Heights, MO, USA.

Mayhew, "Changes in fetal capillaries during preplacental hypoxia: growth, shape remodelling and villous capillarization in placentae from high-altitude pregnancies," Placenta, 2003, pp. 191-198, vol. 24, Elsevier, Maryland Heights, MO, USA.

Reshetnikova, et al., "Placental histomorphometry and morphometric diffusing capacity of the villous membrane in pregnancies complicated by maternal iron-deficiency anemia," American Journal of Obstetrics & Gynecology, 1995, pp. 724-727, vol. 173, Elsevier, Maryland Heights, MO, USA.

Vickers, et al., "Fetal origins of hyperphagia, obesity, and hypertension and postnatal amplification by hypercaloric nutrition," American Journal of Physiology—Endocrinology and Metabolism, 2000, pp. E83-E87, vol. 279,, The American Physiological Society, Bethesda, MD, USA.

Stocker, et al., "Fetal origins of insulin resistance and obesity," Proceedings of the Nutrition Society, 2005, pp. 143-151, vol. 64, Cambridge University Press, New York, NY, USA.

McMillen, et al., "Early origins of obesity: programming the appetite regulatory system," Journal of Physiology, 2005, pp. 9-17, vol. 565, The Physiological Society, Cambridge, UK.

Armitage, et al. "Experimental models of developmental programming: consequences of exposure to an energy rich diet during development," Journal of Physiology, 2005, pp. 3-8, vol. 565, The Physiological Society, Cambridge, UK.

Longo, "Fetal origins of adult vascular dysfunction in mice lacking endothelial nitric oxide synthase," American Journal of Physiology—Regulatory, Integrative and Comparative Physiology, 2005, pp. R1114-R1121, vol. 288, The American Physiological Society, Bethesda, MD, USA.

Horton, "Fetal origins of developmental plasticity: animal models of induced life history variation," Am J Hum Biol, pp. 34-43, 2005, vol. 17.

Bertram, et al., "Prenatal programming of postnatal endocrine responses by glucocorticoids," Reproduction, 2002, pp. 459-467, vol. 124, BioScientifica Ltd, Bradley Stoke, UK.

Green, "Programming of endocrine mechanisms of cardiovascular control and growth," Journal of the Society for Gynecologic Investigation, 2001, pp. 57-68, vol. 8, No. 2, SAGE Publications, Newbury Park, CA, USA.

McMillen, et al. "Developmental origins of the metabolic syndrome: prediction, plasticity, and programming," Physiological Review, 2005, pp. 571-633. vol. 85, The American Physiological Society, Bethesda, MD, USA.

Wu, et al., "Maternal nutrition and fetal development," The Journal of Nutrition, 2004, pp. 2169-2172, vol. 134, American Society for Nutrition, Bethesda, MD, USA.

Pham, et al., "Uteroplacental insufficiency increases apoptosis and alters p53 gene methylation in the full-term IUGR rat kidney," American Journal of Physiology—Regulatory, Integrative and Comparative Physiology, 2003, pp. R962-R970, vol. 285, The American Physiological Society, Bethesda, MD, USA.

Seckl, "Glucocorticoids, feto-placental 11 beta-hydroxysteroid dehydrogenase type 2, and the early life origins of adult disease,". Steroids, 1997, pp. 89-94, vol. 62, Elsevier, Maryland Heights, MO, USA.

Sibley, et al., "Placental phenotypes of intrauterine growth," Pediatric Research, 2005, vol. 58, pp. 827-832, International Pediatric Research Foundation, Inc., Lippincott Williams & Wilkins, Hagerstown MD, USA.

Randhawa, et al., "The role of the insulin-like growth factor system in prenatal growth," Molecular Genetics and Metabolism, 2005, pp. 84-90, vol. 86, Elsevier, Maryland Heights, MO, USA.

Wallace, et al., "Nutritionally mediated placental growth restriction in the growing adolescent: consequences for the fetus," Biology of Reproduction, 2004, pp. 1055-1062, vol. 71, The Society for the Study of Reproduction, Inc., Madison, WI, USA.

(56) References Cited

OTHER PUBLICATIONS

Baschat, et al., "Fetal growth restriction due to placental disease," Seminars in Perinatology, 2004, pp. 67-80, vol. 28, No. 1, Elsevier, Maryland Heights, MO, USA.

Resnik, "Intrauterine growth restriction," Obstetrics & Gynecology, 2002, pp. 490-496, vol. 99, Elsevier, Maryland Heights, MO, USA.

Morley, "Fetal origins of adult disease," Seminars in Fetal & Neonatal Medicine, 2006, pp. 73-78, vol. 11, Elsevier, Maryland Heights, MO, USA.

Lockwood, "The diagnosis of preterm labor and the prediction of preterm delivery," Clinical Obstetrics and Gynecology, 1995, pp. 675-687, vol. 38, No. 4, Lippincott Williams & Wilkins, Hagerstown, MD, USA.

Metzger, et al., "Genetic control of branching morphogenesis," Science Magazine, 1999, pp. 1635-1639, vol. 284, Washington, DC, USA.

Yevtodiyenko, et al., "Dlk1 expression marks developing endothelium and sites of branching morphogenesis in the mouse embryo and placenta," Developmental Dynamics, 2006, pp. 1115-1123, vol. 235, Wiley, Hoboken, NJ, USA.

Le Noble, et al., "Control of arterial branching morphogenesis in embryogenesis: go with the flow," Cardiovascular Research, 2005, vol. 65, pp. 619-628, Elsevier, Maryland Heights, MO, USA.

Warburton, et al., "Molecular mechanisms of early lung specification and branching morphogenesis," Pediatric Research, 2005, pp. 26R-37R, vol. 57, No. 5, pt. 2, Lippincott Williams & Wilkins, Hagerstown MD, USA.

Hu, et al., "Genetic regulation of branching morphogenesis: lessons learned from loss-of-function phenotypes," Pediatric Research, 2003, pp. 433-438, vol. 54, Lippincott Williams & Wilkins, Hagerstown MD, USA.

Ingelfinger, et al., "Perinatal programming, renal development, and adult renal function," American Journal of Hypertension, 2002, pp. 46S-49S vol. 15, No. 2, pt. 2, Elsevier, Maryland Heights, MO, USA.

Miettinen, "Epidermal growth factor receptor in mice and men—any applications to clinical practice?" Annals of Medicine, 1997, pp. 531-534, vol. 29, Informa PLC, St. Helier, Jersey.

Miettinen, et al., "Epithelial immaturity and multiorgan failure in mice lacking epidermal growth factor receptor," Nature, 1995, pp. 337-341, vol. 376, Nature Publishing Group, London, UK.

Grenander, "General Pattern Theory—A Mathematical Study of Regular Structures," 1993, pp. 539-544 and 740-784, Oxford University Press, Oxford, UK.

Amit, et al., "Structural image restoration through deformable templates,". Journal of the American Statistical Association, 1991, pp. 376-387, vol. 86, No. 414, American Statistical Association, Alexandria, VA, USA.

Grizzi, et al., "Estimate of Neovascular Tree Complexity by Microscopy Analysis," Current Issues on Multidisciplinary Microscopy Research and Education, 2005, pp. 140-148, Formatex, Badajoz, Spain.

Giles, "Benoit Mandelbrot: father of fractals," Nature, 2004, pp. 266-267, vol. 432, Nature Publishing Group, London, UK.

Meisel, "Generalized Mandelbrot rule for fractal sections," Physical Review A, 1992, pp. 654-656, vol. 45, No. 2, American Physical Society, College Park, MD, USA.

Keipes, et al., "Of the British coastline and the interest of fractals in medicine," Biomedicine & Pharmacotherapy, 1993, pp. 409-415, vol. 47, Elsevier, Maryland Heights, MO, USA.

Porter, et al., "A fractal analysis of pyramidal neurons in mammalian motor cortex," Neuroscience Letters, 1991, pp. 112-116, vol. 130, Elsevier, Maryland Heights, MO, USA.

Mayhew, et al., "Stereological investigation of placental morphology in pregnancies complicated by pre-eclampsia with and without intrauterine growth restriction," Placenta, 2003, pp. 219-226, vol. 24, Elsevier, Maryland Heights, MO, USA.

Byrne, "Factor analytic models: viewing the structure of an assessment instrument from three perspectives," Journal of Personality Assessment, 2005, pp. 17-32, vol. 85, Informa PLC, St. Helier, Jersey.

Coste, et al., "Methodological issues in determining the dimensionality of composite health measures using principal component analysis: case illustration and suggestions for practice," Quality of Life Research, 2005, pp. 641-654, vol. 14, Springer, New York, NY, USA.

Bentler, et al., "Structural equation models in medical research," Statistical Methods in Medical Research, 1992, pp. 159-181, vol. 1, SAGE Publications, Newbury Park, CA, USA.

Pembrey, "The Avon Longitudinal Study of Parents and Children (ALSPAC): a resource for genetic epidemiology," European Journal of Endocrinology, 2004, pp. U125-U129, vol. 151, BioScientifica Ltd, Bristol, UK.

Patel, et al., "Prenatal risk factors for Caesarean section. Analyses of the ALSPAC cohort of 12,944 women in England," International Journal of Epidemiology, 2005, pp. 353-367, vol. 34, Oxford University Press, Oxford, UK.

Headley, et al., "Medication use during pregnancy: data from the Avon Longitudinal Study of Parents and Children," European Journal of Clinical Pharmacology, 2004, pp. 355-361, vol. 60, Springer, New York, NY, USA.

Fergusson, et al., "Maternal use of cannabis and pregnancy outcome," BJOG: An International Journal of Obstetrics and Gynaecology, 2002, pp. 21-27, vol. 109, Wiley, Hoboken, NJ, USA.

Golding, "Outcome of pregnancy in diabetic women—more investigation is needed into whether control of diabetes is really poorer in England than Norway," BMJ, 2001, pp. 614-615, vol. 322, BMJ Group, London, UK.

Dorosty, et al., "Factors associated with early adiposity rebound," Pediatrics, 2000, pp. 1115-1118, vol. 105, American Academy of Pediatrics, Elk Grove Village, IL, USA.

Rogers, et al., "Financial difficulties, smoking habits, composition of the diet and birthweight in a population of pregnant women in the South West of England," European Journal of Clinical Nutrition, 1998, pp. 251-260, vol. 52, Nature Publishing Group, London, UK.

Farrow, et al., "Birthweight of term infants and maternal occupation in a prospective cohort of pregnant women," Occupational and Environmental Medicine, 1998, pp. 18-23, vol. 55, BMJ Group, London, UK.

Maitra, et al., "Mode of delivery is not associated with asthma or atopy in childhood," Clinical and Experimental Allergy, 2004, pp. 1349-1355, vol. 34, Wiley, Hoboken, NJ, USA.

Golding, "Children of the nineties—a longitudinal study of pregnancy and childhood based on the population of Avon (ALSPAC)," West of England Medical Journal, 1990, pp. 80-82, vol. 105.

Carey, "Infant Temperament Questionnaire (4-8 months)," Philadelphia: Dept. Educational Psychology, Temple University, 1977.

Fullard, et al., "Toddler Tempermant Scale (1-3 year old children)" Philadelphia, PA: Dept. Educational Psychology, Temple University, 1978.

Buss, et al., "The EAS Temperament Scale," in Temperament: Early Developing Personality Traits, 1984, Hillsdale, NJ, USA.

Goodman, "The Strengths and Difficulties Questionnaire: a Research Note . . . ," Journal of Child Psychology and Psychiatry, 1997, pp. 581-586, vol. 38, No. 5, Wiley, Hoboken, NJ, USA.

Frankenburg, et al., "The Denver Developmental Screening Test," Journal of Pediatrics, 1967, pp. 181-191, vol. 71, No. 2, Elsevier, Maryland Heights, MO, USA.

Salafia, C.M., et al., Intrauterine growth restriction in infants of less than thirty-two weeks' gestation: associated placental pathologic features. Am Journal Obstet Gynecol, 1995. 173(4): pp. 1049-1057.

Salafia, C.M., et al., Maternal, placental, and neonatal associations with early germinal matrix/intraventricular hemorrhage in infants born before 32 weeks' gestation. Am Journal Perinatol, 1995. 12(6): pp. 429-436.

Salafia, C.M., et al., Clinical correlations of patterns of placental pathology in preterm pre-eclampsia. Placenta, 1998. 19(1): pp. 67-72.

Salafia, C.M., et al., Placental pathologic features of preterm preeclampsia. Am Journal Obstet Gynecol, 1995. 173 (4): pp. 1097-1005.

Salafia, C.M., et al., Placental pathology of absent and reversed end-diastolic flow in growth-restricted fetuses. Obstet Gynecol, 1997. 90(5): pp. 830-836.

(56) References Cited

OTHER PUBLICATIONS

Viscardi, R.M. and C.C. Sun, Placental lesion multiplicity: risk factor for IUGR and neonatal cranial ultrasound abnormalities. Early Hum Dev, 2001.62(1): pp. 1-10.

Hagberg, H., D. Peebles, and C. Mallard, Models of white matter injury: comparison of infectious, hypoxic-ischemic, and excitotoxic insults. Ment Retard Dev Disabil Res Rev, 2002. 8(1): pp. 30-38.

Kuh et al., "A life course approach to women's health. Life course approach to adult health". No. 1. 2002, pp. 419, Oxford; New York: Oxford University Press.

Myrianthopoulos, N.C. and K.S. French, An application of the U.S. Bureau of the Census socioeconomic index to a large, diversified patient population. Soc Sci Med, 1968. 2(3): pp. 283-299.

Johansson, et al., "System for Integrated Interstitial Photodynamic Therapy and Dosimetric Monitoring", Proceedings of the Spie—The International Society for Optical Engineering, Jan. 2005, pp. 130-140, vol. 5689, No. 1.

Benirschke, "Architecture of Normal Villous Trees," Chapter 7 in Pathology of the Human Placenta, 2002, pp. 121-173, Springer, New York, NY, USA.

K. B., Examination of the Placenta, prepared for the Collaborative Study on Cerebral Palsy, Mental retardation and other Neurological and Sensory Disorders of Infancy and Childhood, N.I.o.N.D.a. Blindness, Editor. 1961, US Department of Health, Education and Welfare.

Fink, "Computer Simulation of Pressure Fields Generated by Acoustic Lens Beamformers", 1994, University of Washington, Seattle, WA.

Griffiths, "Administering the Scale, in The Abilities of Babies—A Study in Mental Measurement", 1954, pp. 117-182, McGraw-Hill, New York, NY, USA.

Fenson, et al., "Technical Manual for the MacArthur Communicative Development Inventories," 1991, San Diego, CA: Development Psychology Laboratory.

Miller, et al., "A Mathematical textbook of deformable neuro-anatomies . . . ," Proceedings of the National Academy of Sciences, 1993, pp. 11944-11948, National Academy of Sciences, Washington, DC, USA.

Hastie, et al., "Elements of Statistical Learning: Data Mining, Inference, and Prediction," 2001, pp. 1-40, Springer, New York, NY, USA.

Penev, et al., "Local feature analysis: a general statistical theory for object representation . . . ," Network: Computation in Neural Systems, 1996, pp. 477-500, vol. 7, Informa PLC, St. Helier, Jersey.

Small, C., The Statistical Theory of Shape. 1996, New York: Springer.

Dryden, I.L.M., KV., Statistical Shape Analysis. 1998, New York: Wiley Press.

Lele, S.R., JT., An Invariant Approach to Statistical Analysis of Shapes. 2000, London, UK.: Chapman and Hall/CRC Press.

McKeague, I., A Statistical Model for Signature Verification . . . Journal of the American Statistical Association, 2005. 100: p. 231-241.

Benirschke K, K.P., Normative Values and Tables (Chapter 28), in Pathology of the Human Placenta. 2002, Springer-Verlag: New York. p. 920-927.

Salafia, et al., "Relationship between placental histologic features and umbilical cord blood gases in preterm gestations," American Journal of Obstetrics & Gynecology, 1995, pp. 1058-1064, vol. 173, Elsevier, Maryland Heights, MO, USA.

Salafia, C.M., et al., "Intrauterine growth restriction in infants of less than thirty-two weeks' gestation: associated placental pathologic features". American Journal of Obstetric Gynecology, 1995, pp. 1049-1057, vol. 173 No. 4.

Salafia, C.M., et al, "Maternal, placental, and neonatal associations with early germinal matrix/intraventricular hemorrhage in infants born before 32 weeks' gestation". American Journal of Perinatology, 1995, pp. 429-436, vol. 12, No. 6.

Salafia, C.M., et al., "Placental pathologic features of preterm preeclampsia". American Journal of Obstetric Gynecoloogy, 1995. pp. 1097-1105, vol. 173, No. 4.

Salafia, C.M., et al., "Clinical correlations of patterns of placental pathology in preterm pre-eclampsia". Placenta, 1998. pp. 67-72, vol. 19, No. 1.

Salafia, C.M., et al., "Placental pathology of absent and reversed end-diastolic flow in growth-restricted fetuses". Obstetric Gynecology, 1997, pp. 830-836, vol. 90, No. 5.

Viscardi, et al., "Placental lesion multiplicity: risk factor for IUGR and neonatal cranial ultrasound abnormalities". Early Human Development, 2001. pp. 1-10, vol. 62, No. 1.

Hagberg, et al., "Models of white matter injury: comparison of infectious, hypoxic-ischemic, and excitotoxic insults". Mental Retardation Developmental Disability Research Review, 2002. pp. 30-38, vol. 8, No. 1.

Benirschke B., "Examination of the Placenta". Prepared for the Collaborative Study on Cerebral Palsy, Mental retardation and other Neurological and Sensory Disorders of Infancy and Childhood, N.I.o.N.D.a. Blindness, Editor. 1961, US Department of Health, Education and Welfare.

Kuh, D. and R. Hardy, A life course approach to women's health. Life course approach to adult health ; No. 1. 2002, Oxford ; New York: Oxford University Press. xvi, 419 p.

Niswander, et al., "The Collaborative Perinatal Study of the National Institute of Neurological Diseases and Stroke: The Women and Their Pregnancies". 1972, Ch. 1-4 and 11, Philadelphia, PA: W.B. Saunders.

Myrianthopoulos et al., "An application of the U.S. Bureau of the Census socioeconomic index to a large, diversified patient population". Social Science & Medicine, 1968, pp. 283-299, vol. 2 No. 3.

Baik, I., et al., Association of fetal hormone levels with stem cell potential: evidence for early life roots of human cancer. Cancer Res, 2005. 65(1): p. 358-63.

Lagiou, P., et al., Birthweight differences between USA and China and their relevance to breast cancer aetiology. Int J Epidemiol, 2003. 32(2): p. 193-8.

Examiner's First Report on related Australian Patent Application No. 2005280762 dated Apr. 14, 2010 (2 pgs).

Warren, Paul. "From Ubiquitous Computing to Ubiquitous Intelligence," Journal BT Technology, Springer Netherlands, Issue vol. 22, No. 2/Apr. 2004, pp. 28-38 [retireved on Jul. 2, 2007]. Retrieved from the Internet: URL: http://www.tcn-uk.org/siteassets/documents/TCN/1/B/1BB94F36-032A-47D4-BC1E-336FABCC 40C8/1/2004%20vol3prt1%20Jan%20(5).pdf>.

International Search Report for PCT/US07/08870 dated Jan. 8, 2008 (2 pgs).

International Search Report and Written Opinion for PCT/US06/1682 dated Sep. 21, 2007 (7 pgs).

International Search Report and Written Opinion International Application No. PCT/US2009/051017 dated Dec. 28, 2010.

Castellucci, et al., "Basic Structure of the Villous Trees," Chapter 6 in The Pathology of the Placenta, 2002, pp. 50-120, Springer, New York, NY, USA.

Baik, et al., "Association of fetal hormone levels with stem cell potential: evidence for early life roots of human cancer," Cancer Research, 2005, pp. 358-363, vol. 65, No. 1, American Association for Cancer Research, Philadelphia, PA USA.

Lagiou, et al., "Birthweight differences between USA and China and their relevance to breast cancer aetiology," International Journal of Epidemiology, 2003, pp. 193-198, vol. 32, Oxford University Press, Oxford, UK.

Horton, "Fetal origins of developmental plasticity: animal models of induced life history variation," America Journal of Human Biology, 2005, pp. 34-43, vol. 17, Wiley, Hoboken, NJ, USA.

Resnik, "Intrauterine growth restriction," Obstetrics & Gynecology, 2002,, pp. 490-496, vol. 99, Elsevier, Maryland Heights, MO, USA.

Carey, et al., "Revision of the Infant Temperament Questionnaire," Pediatrics, 1978, pp. 735-739, vol. 61, No. 5, American Academy of Pediatrics, Elk Grove Village, IL, USA.

Fullard, et al., "Assessing Temperament in One- to Three-Year-Old Children," Journal of Pediatric Psychology, 1984, pp. 205-217, vol. 9, No. 2, Oxford University Press, Oxford, UK.

Buss, et al., "Behavioral Genetics," in Temperament: Early Developing Personality Traits, 1984, pp. 105-117, Lawrence Erlbaum Associates, Hillsdale, NJ, USA.

(56) References Cited

OTHER PUBLICATIONS

Rich-Edwards, et al., "Longitudinal study of birth weight and adult body mass index in predicting risk of coronary heart disease and stroke in women," BMJ Online First, 2005, pp. 1-6, BMJ, London, UK.

Benirschke, "Classification of Villous Maldevelopment," Chapter 15, in Pathology of the Human Placenta, 2002, pp. 491-518, Springer, New York, NY, USA.

Goodman, "The Strengths and Difficulties Questionnaire: a Research Note," Journal of Child Psychology and Psychiatry, 1997, pp. 581-586, vol. 38, No. 5, Wiley, Hoboken, NJ, USA.

Fenson, et al., MacArthur-Bates Communicative Development Inventories—User's Guide Technical Manual, 2007, pp. 15-46 and 151-161, Paul H. Brookes Publishing Co., Baltimore, MD, USA.

Miller, et al., "Mathematical textbook of deformable neuroanatomies," Proceedings of the National Academy of Sciences, 1993, pp. 11944-11948, National Academy of Sciences, Washington, DC, USA.

Hastie, et al., "The Elements of Statistical Learning—Data Mining, Inference, and Prediction," 2001, pp. 1-40, Springer, New York, NY, USA.

Penev, et al., "Local feature analysis: a general statistical theory for object representation," Network: Computation in Neural Systems, 1996, pp. 477-500, Informa PLC, St. Helier, Jersey.

Small, "The Statistical Theory of Shape," 1996, pp. 66-116, Springer, New York, NY, USA.

Dryden, et al., "Statistical Shape Analysis," 1998, pp. 251-290, Wiley, Hoboken, NJ, USA.

Lele, et al., "An Invariant Approach to Statistical Analysis of Shapes," 2000, pp. 215-244, Chapman and Hall/CRC Press, London, UK.

McKeague, "A Statistical Model for Signature Verification," Journal of the American Statistical Association, Mar. 2005, pp. 231-241, American Statistical Association, Alexandria, VA, USA.

Benirschke, "Normative Values and Tables," in Pathology of the Human Placenta, 2002, pp. 1019-1026, Springer, New York, NY, USA.

Wei, Yadong et al., "Photoacouslic tomography imaging using a 4f acoustic lens and peak-hold technology", School of Physics and Telecom Engineering, South China Normal University 51006, Guangzhou, China, Apr. 14, 2008/ vol. 16, No. 8/ Optics Express 5314-5319.

LOW-COST DEVICE FOR C-SCAN ACOUSTIC WAVE IMAGING

REFERENCE TO RELATED APPLICATION

The present application is a Continuation of U.S. patent application Ser. No. 12/505,264 filed Jul. 17, 2009, now U.S. Pat. No. 8,353,833, which claims the benefit of U.S. Provisional Patent Application No. 61/081,946, filed Jul. 18, 2008, the disclosures of which are each hereby incorporated by reference in their entirety.

FIELD OF THE INVENTION

The present invention is directed to imaging, e.g., of prostate tissue for detection of cancer and more particularly to photoacoustic imaging and ultrasound imaging to produce C-scans.

DESCRIPTION OF RELATED ART

Prostate cancer is the most prevalent newly diagnosed malignancy in men, second only to lung cancer in causing cancer-related deaths. Adenocarcinoma of the prostate is the most common malignancy in the Western world. There were a projected 218,890 new cases of prostate cancer diagnosed in the United States in 2007, with an estimated 27,050 deaths. As men age, the risk of developing prostate cancer increases. Prostate cancer has been found incidentally in approximately 30% of autopsy specimens of men in their sixth decade. Seventy to 80% of patients who have prostate cancer are older than 65 years. Clinically localized disease is usually suspected based on an elevated prostate specific antigen (PSA) test or abnormal digital rectal exam (DRE), prompting transrectal ultrasound (TRUS) guided biopsy of the prostate for definitive diagnosis. TRUS however, is not reliable enough to be used solely as a template for biopsy. There are cancers that are not visible (isoechoic) on TRUS. Furthermore, in PSA screened populations, the accuracy of TRUS was only 52% due to false-positive findings encountered. Increased tumor vessels (angiogenesis) have been shown microscopically in prostate cancer compared with benign prostate tissue. Efficacy of color and power Doppler ultrasound has not been demonstrated, probably due to limited resolution and small flow velocities. Elasticity imaging, with its many variants, is a new modality that is currently under extensive investigation. It is evident that given the limitations of the present diagnostic protocols, development of a new imaging modality that improves visualization and biopsy yield of prostate cancer would be beneficial. Furthermore, by making it cost effective, we can place it in the hands of primary care physicians, where it will serve its primary purpose as an adjunct to PSA, DRE, and TRUS.

The need for tumor visualization is equally critical in the treatment of localized prostate cancer disease. Existing therapeutic strategies, namely external beam radiation, prostate brachytherapy, cryosurgery, and watchful waiting, all will benefit significantly from the development of a new modality that promises better tumor contrast. Thus, prostate cancer continues to be an area in which progress is needed despite recent advancements.

Appropriate imaging of prostate cancer is a crucial component for diagnosing prostate cancer and its staging, in addition to PSA levels and DRE. The current state of prostate imaging for diagnosis of prostate cancer includes ultrasound, ultrasound-guided prostate biopsies, magnetic resonance imaging (MRI), and nuclear scinitigraphy. These modalities are helpful, but have drawbacks and limitations. MRI is expensive and not mobile. Nuclear scintillation is expensive, provides low resolution planar images, and there are problems with radiotracer excretion through the kidneys. Both these modalities are not available for general use.

Ultrasound is not reliable enough to use solely as a template for diagnosing prostate cancer. It has two problems. First, in many cases prostate cancer appears as an isoechoic lesion (similar gray scale value as surrounding tissue) causing high miss rate (FIG. 10). Secondly, when it is visible (hyper or hypoechoic), it is not possible to say with certainty if it is cancer or benign because many other noncancer conditions such as prostate atrophy, inflammation of the prostate gland, and benign tumors may also look similar in appearance on ultrasound examination. A biopsy has to be performed on the suspect lesion for definitive diagnosis. Biopsies are uncomfortable and bleeding may result as a complication. Because of poor lesion detection, even the current prostate biopsy techniques miss approximately 30% of prostate cancer. Utility of color flow and power Doppler in conjunction with gray scale ultrasound has been explored, but not successfully. Therefore, there is an urgent need for a new imaging methodology that will be portable, economical to build, and will have widespread utility as a tool for primary screening and diagnosis of prostate cancer.

FIG. 10 shows transrectal sonography of the prostate gland with confirmed prostate cancer. FIG. 10 demonstrates the grayscale appearance of the prostate gland (within arrows) in a patient with confirmed multiple zones of prostate cancer. As shown, the whole prostate gland appears heterogeneous and the prostate cancer zone is not identifiable because prostate cancer is similar in appearance to the surrounding prostate gland tissue. The arrowheads correspond to calcifications that can be seen in the prostate gland.

U.S. Patent Application Publication No. US 2009/0024038 A1 to Arnold teaches an acoustic imaging probe incorporating photoacoustic excitation, but does not overcome all of the above-noted deficiencies of the prior art.

SUMMARY OF THE INVENTION

It is therefore an object of the invention to provide photoacoustic (PA) imaging technology for the betterment of prostate cancer diagnosis and disease management.

It is a further object of the invention to provide a low-cost imaging technology that can take C-scan images of the prostate gland in real time based on the photoacoustic phenomenon.

It is a yet further object of the invention to provide a low-cost imaging technology that can take C-scan images based on both the photoacoustic phenomenon and ultrasound so that the resulting images are automatically coregistered.

It is a still further object of the invention to provide such a low-cost imaging technology whose applicability is not limited to prostate cancer, but instead can be extended to other organs for cancer detection such as breast cancer, uterine cancer, ovarian cancer, thyroid cancer, etc.

To achieve the above and other objects, the present invention is directed to an imaging technology combining C-scans with the photoacoustic effect. C-scans are two-dimensional (2D) images produced by digitizing the point-by-point signal variation of an interrogating sensor while it is scanned over the surface. The x-y position of the sensor is recorded simultaneously with signal variations. A computer converts point-by-point data into an appropriate image.

The photoacoustic effect is a phenomenon where acoustic waves are produced by absorbing points or objects of a medium that is irradiated with low-energy nanosecond (ns) pulses of laser light usually in near infrared region (NIR). The absorption of a short optical pulse causes localized heating and rapid thermal expansion, which generates thermoelastic stress waves (ultrasound waves). The ultrasound waves are generated instantaneously and simultaneously everywhere in a three-dimensional (3D) tissue volume irradiated by the laser pulse. The frequency content of the ultrasound waves generated is usually 1 to 20 MHz. It propagates in tissue as spherical waves in all directions. These waves will be referred to as the "PA signal" herein.

In this methodology, the prostate gland will be stimulated with laser light, resulting in ultrasound waves (photoacoustic effect) that will be focused by an acoustic lens and captured by a specific 2D sensor array and subsequently displayed as a C-scan on a computer screen. The amplitude of the ultrasound waves generated by laser stimulation is proportional to the optical absorption of the tissue element at that spatial location. Variability in tissue absorption results in C-scan image contrast. For example, optical absorption in blood is 10-100 times higher than prostate tissue in the near infrared region. On this basis it is believed that the ultrasound signature in the C-scan image from prostate cancer will be different than the rest of the prostate gland. It is non echo-based imaging because there is no transmitted ultrasound pulse and contrast in the image does not depend on the echogenicity. Therefore, it is more advantageous than conventional ultrasound because it is based on a different contrast mechanism. It may be considered a hybrid imaging technique, combining ultrasound for imaging and photoacoustic effect for contrast.

The key task in PA imaging is to determine the laser absorption distribution from the measured PA signal data. Most of the existing methodologies are slow (because the sensor acquires data point-by-point), computationally intensive (because computer based algorithms have to be used to reconstruct the image), suffer from poor SNR, and are expensive to develop and market. Lens focusing of sound energy generated with photoacoustic stimulation will improve the SNR and will project reconstructed coronal plane images (C-scan) of the prostate gland simultaneously.

The imaging system can be lightweight, small in size, and therefore portable. The entire lens and sensor assembly can fit in a capsule no larger than 1.5×1×1 inches that can be used transrectally. A low power laser source and a computer monitor is all that will be required externally.

The electrical power consumption of the invention, which in at least one embodiment is called "Low Cost Device for C-Scan Photoacoustic Imaging of Prostate Gland Cancer" (CSPIP), will be very low because, unlike other existing methodologies under development, lens focusing does not require any electrical power. CSPIP has the potential for near real-time imaging (30 frames per second) unlike other methodologies, because they require some computational time for image reconstruction before it can be displayed. In CSPIP the lens forms a focused image that will be read out with the specially designed sensor at video rates (20-30 frames per second). CSPIP also offers the potential for full 3 dimensional imaging of the prostate through development of zoom acoustical lenses that will enable full resolution z-axis image cataloging and reconstruction as a solid. This will enhance the probability of early detection by enabling an arbitrary number of viewing angles of the prostate structure on the computer screen. Additionally this will also help in prostate cancer therapy planning and management (Radiotherapy and Brachytherapy-radioactive seed implantation).

The invention has great potential to exploit high contrast in laser NIR absorption between blood and prostate tissue. Angiogenesis (increased tumor blood vessels) of prostate cancer is well established. Therefore, it is believed that we will be able to visualize the cancer and its size better with CSPIP than with transrectal ultrasound (TRUS), because the latter is based only on the echogenicity of cancer tissue.

CSPIP may also prove to be unique and better than Doppler ultrasound in detecting angiogenesis, because Doppler flow has poor detection sensitivity for slow flow velocities. In CSPIP, contrast in the image depends on the blood concentration in cancer tissue and not on the blood flow velocity; therefore, it is expected to have better contrast and improved delineation of prostate cancer.

In summary, CSPIP for prostate cancer detection we have proposed overcomes many shortcomings of the existing methodologies for imaging prostate cancer. It is a low cost, portable, non-echo based device that works on laser NIR stimulation followed by lens-based focusing of the PA signal. In CSPIP images are generated secondary to photoacoustic stimulation of the prostate gland. This system will have better contrast resolution than conventional ultrasound for detection of prostate cancer.

Various detector arrays can be used, including 1D and 2D arrays.

The present invention differs from that of the Arnold reference at least in terms of time gating. The present invention uses time gating to select acoustic signals coming from a particular depth and thereby to provide a C-scan. Since Arnold does not use time gating, it cannot produce a C-scan.

BRIEF DESCRIPTION OF THE DRAWINGS

Preferred embodiments of the present invention will be set forth in detail with respect to the drawings, in which.

DETAILED DESCRIPTION OF THE PREFERRED EMBODIMENT

Figure 1:
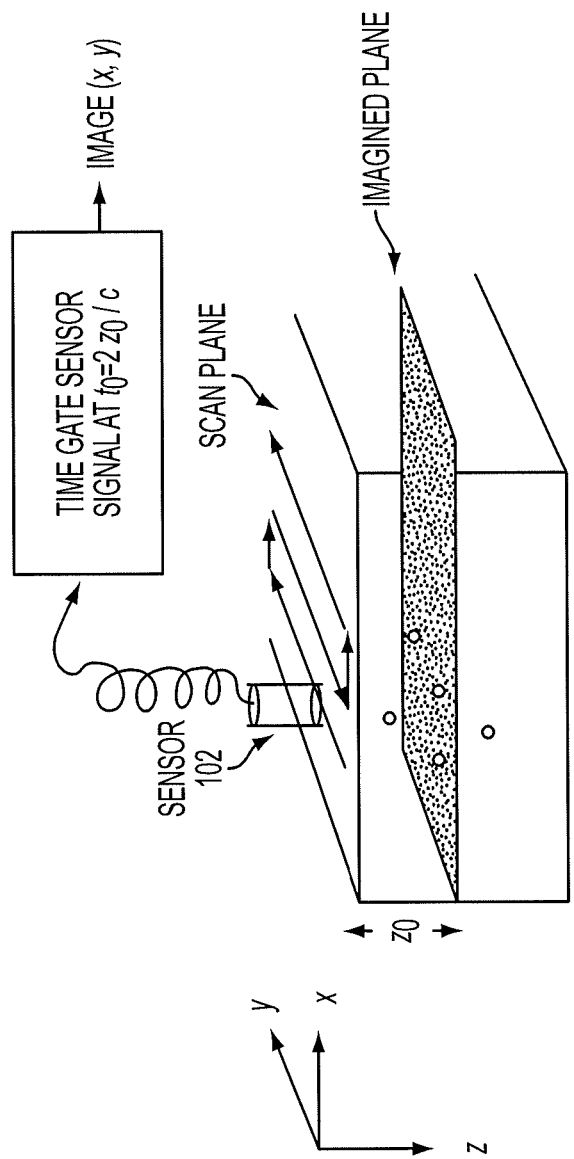
FIG. 1 is a concept diagram to illustrate the concept of C-scan.

Preferred embodiments of the present invention will be set forth in detail with reference to the drawings, in which like reference numerals refer to like elements or steps throughout.

FIG. 1 shows C-scan with an ultrasound sensor 102, which is scanned in a scan plane $P_S$ to perform imaging in an imaged plane $P_I$ to produce a signal S from which an image I is reconstructed. From the travel time of the sound waves one can determine the depth z of the reflector or scatterer R, because the speed of sound c is known. Therefore, if we record the sensor signal amplitude at a fixed time $t_0 = 2z_0/c$ and scan it point-by-point in the x-y plane as shown, we essentially image the imaged or object plane $P_I$ at depth $z_0$. This is referred to as the C-scan planer image at depth $z_0$.

The PA signal at each pixel is proportional to the incident laser flux and the absorption coefficient of the tissue. Because the absorption coefficient of tissue depends on the laser wavelength, experiments will be performed to determine the best wavelength for optimal contrast in the PA image. Laser wavelengths to be used will be in the near infrared region.

Figure 2:
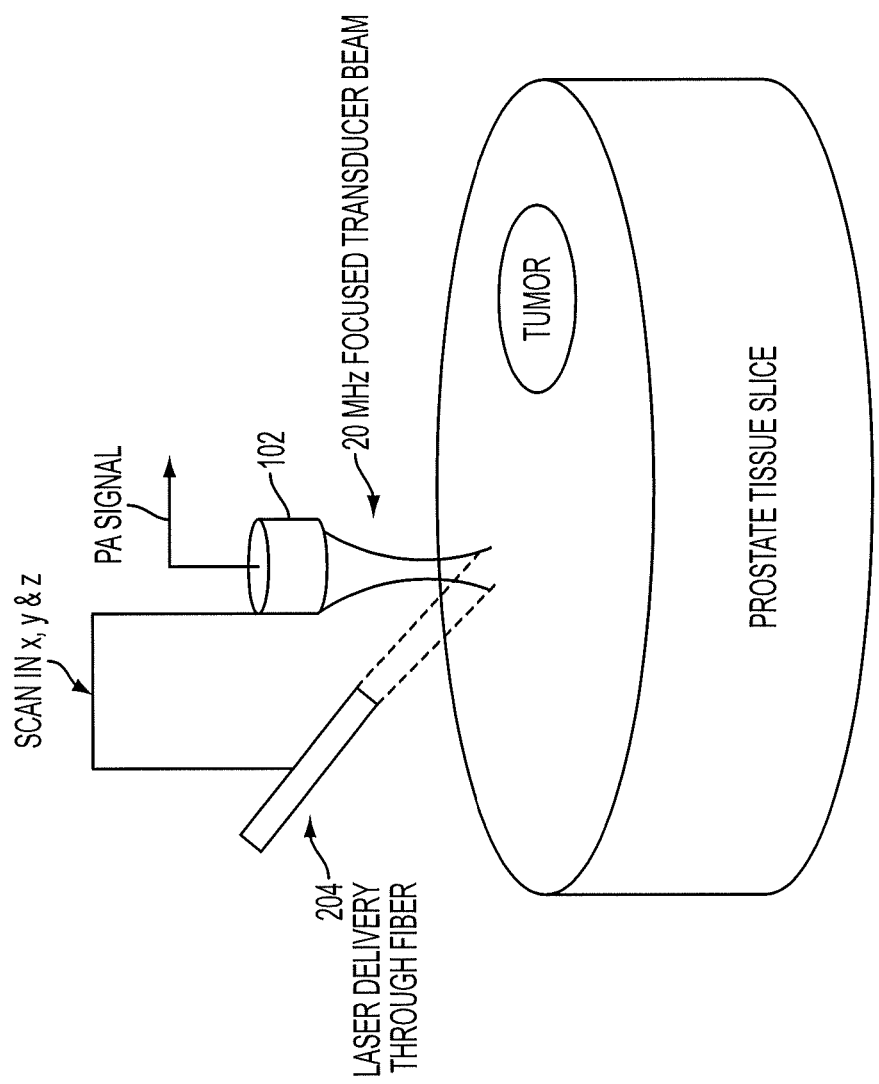
FIG. 2 is a diagram of a stage-1 experiment.

FIG. 2 shows the schematics for the experimental setup. Freshly excised prostate tissue slices of 2-4 mm will be immersed in a saline solution bath. A 10 ns laser pulse at a fixed wavelength λ will be delivered to a small spot (approximate diameter 100 microns) via a fiber optic cable 204.

According to the American National Standards Institute (ANSI), maximum permissible exposure for human skin is 100 mJ/cm². Laser flux will be kept below this limit at all times. A 20 MHz, 6 mm diameter circular disk transducer with a focal length of 12 mm will be used as a sensor for the PA signal. The transducer focal spot is expected to be 100 microns and will overlap with the laser spot. This overlap region is expected to set the spatial resolution for these experiments. The laser-transducer rigid assembly will be scanned in x-y and z directions with stepper motors under computer control. The step size may vary from 10-50 microns. At each pixel location, the time-gated high frequency PA ultrasound signal will be digitized at 100 MHz and stored for further processing. The time gating can be performed in, or under the control of, a processor by any suitable technique. PA images will be created using several different data extraction schemes applied to the signal captured at each pixel location; they include (i) peak signal value in the time gate (ii) total energy in the time gate, and (iii) Amplitudes at several different temporal frequencies in the PA signal derived via its Fourier transform. These stage 1 experiments will enable determination of the optimal laser wavelength to be used for PA imaging.

The objective of stage 2 is to finalize the preliminary acoustic lens and hand-held device design generated by and to fabricate and test its ability to produce C-scan planar PA images of the prostate gland in-vitro.

Figure 3:
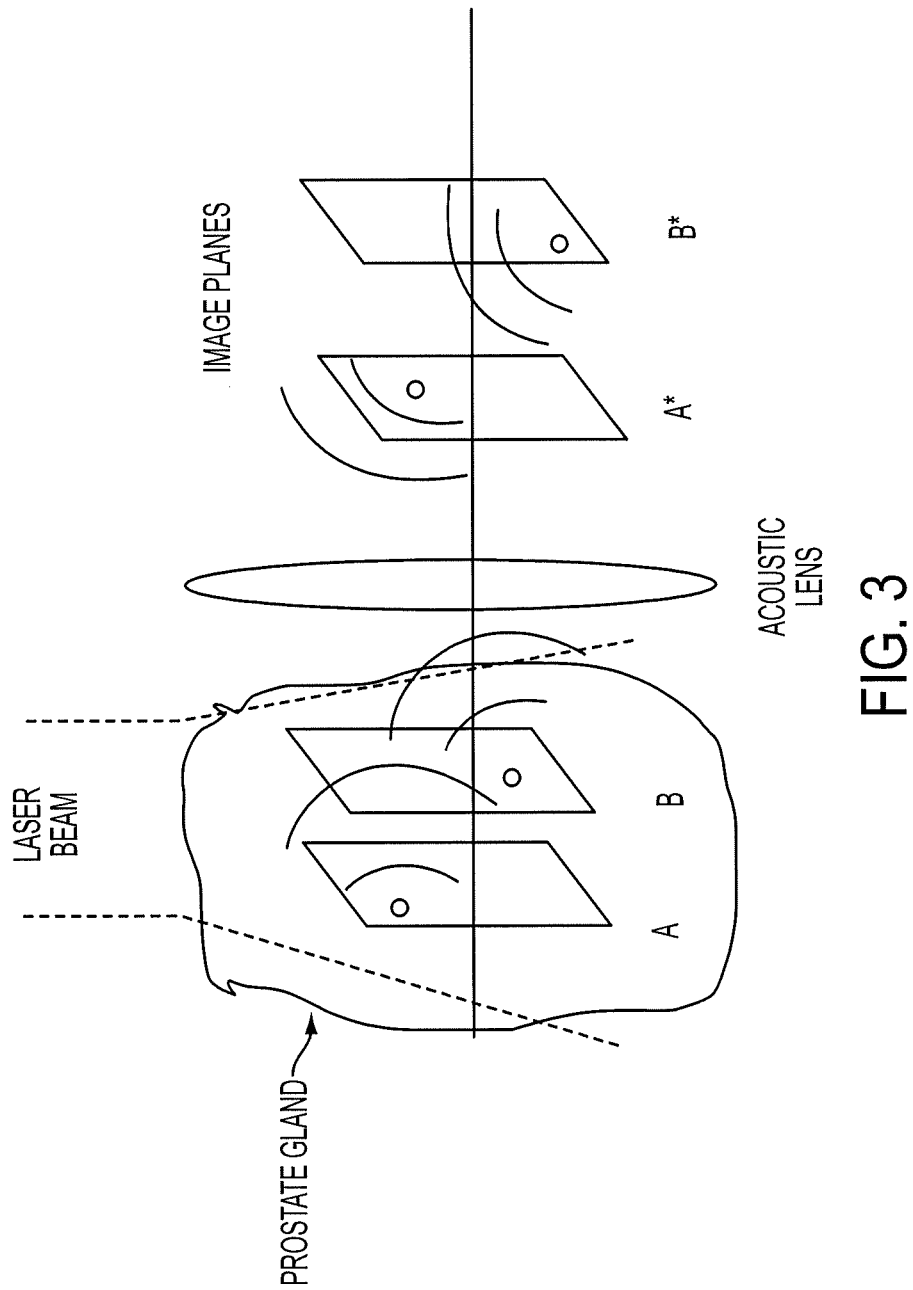
FIG. 3 is a diagram of a stage-2 experiment.

FIG. 3 is a concept diagram that explains the innovative approach to PA imaging and the setup for the stage 2 experiments. Consider a nanosecond laser beam that irradiates the object at time t=0. Let there be two point absorbers in plane A and B, respectively. The PA transient wave fronts are shown diverging from the points. The idea is to focus these PA transient wavefronts with an acoustic lens system 306, much like optical focusing of light waves for optical image formation. An appropriately designed lens will converge the wavefronts from the point in plane A to the point in plane A* and the point in plane B to point in plane B* respectively.

A sensor located in plane A* can capture this energy as a focused image. It takes approximately 6.5 microseconds for ultrasound to travel 1 cm in tissue. It has been shown that the PA transient time signal is typically 1 microsecond or less in duration. Therefore, by time gating the total signal we can discard or minimize the signal coming from planes that are separated more than 1.5 mm from the chosen plane of focus. The assumption here is that the signal from all points in plane A comes to a focus in plane A* and its arrival time will be within the selected time gate width. The signal from all other planes will be discriminated primarily due to the time gate and secondarily due to the spatial spreading of its energy on this sensor plane that does not happen to be their corresponding conjugate image plane.

Figure 5A:
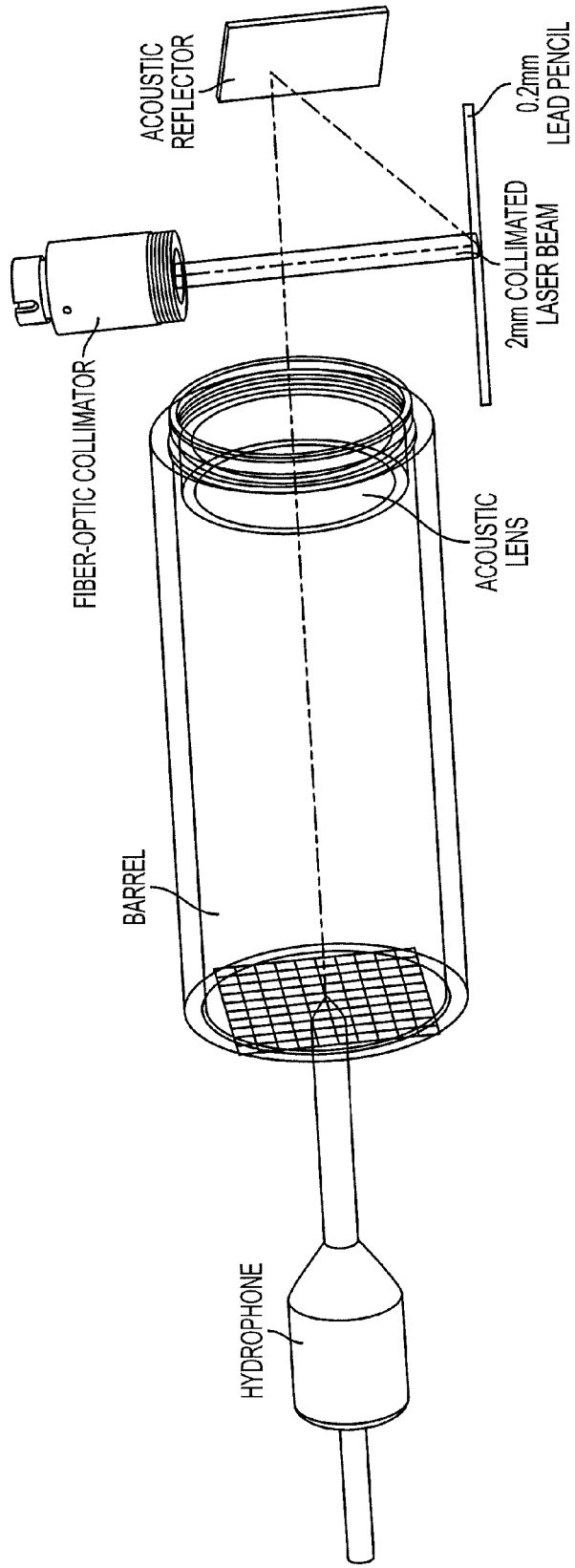
FIG. 5A shows a lens-based C-scan photoacoustic imaging breadboard proof of concept.

Tests of the concept will be described. FIG. 5A shows the setup. The image plane was scanned with a 1.5 mm diameter hydrophone. C-scan image plane was 10×25 pixels. The object was 0.2 mm lead pencil illuminated by a laser beam of 2 mm diameter. The laser generated pulses of wavelength 1064 nm with 10 ns pulse width. The point object was located at an object distance (OD) from the lens. The lens had a focal length of 27.5 mm. Hydrophone was located in the image plane at an image distance (ID) from the lens. An acoustic reflector was used to simulate first embodiment of prostate probe.

Figure 4:
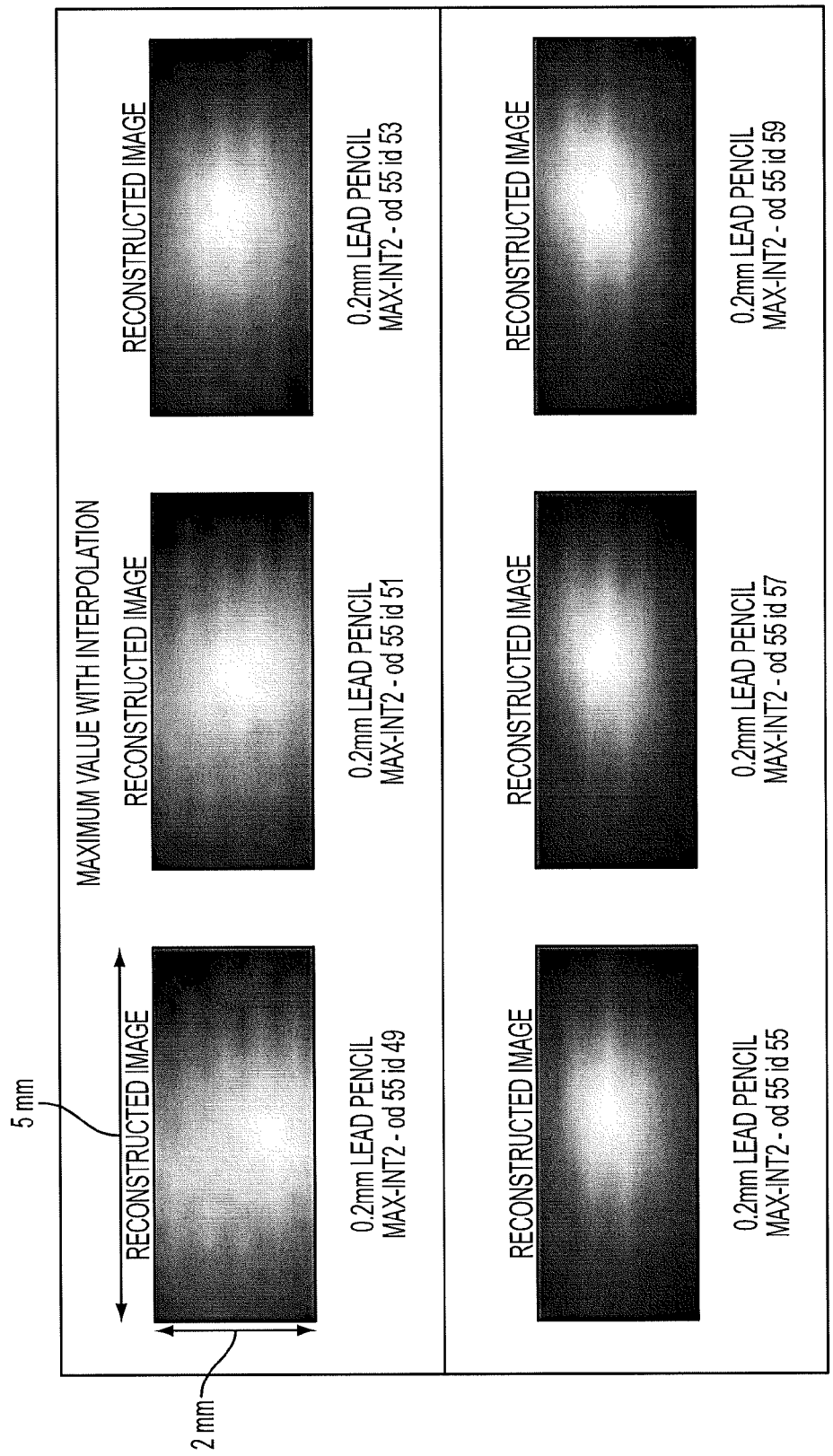
FIG. 4 shows a set of C-scan photoacoustic images of a pencil exposed by a 2 mm laser beam.
Figure 5B:
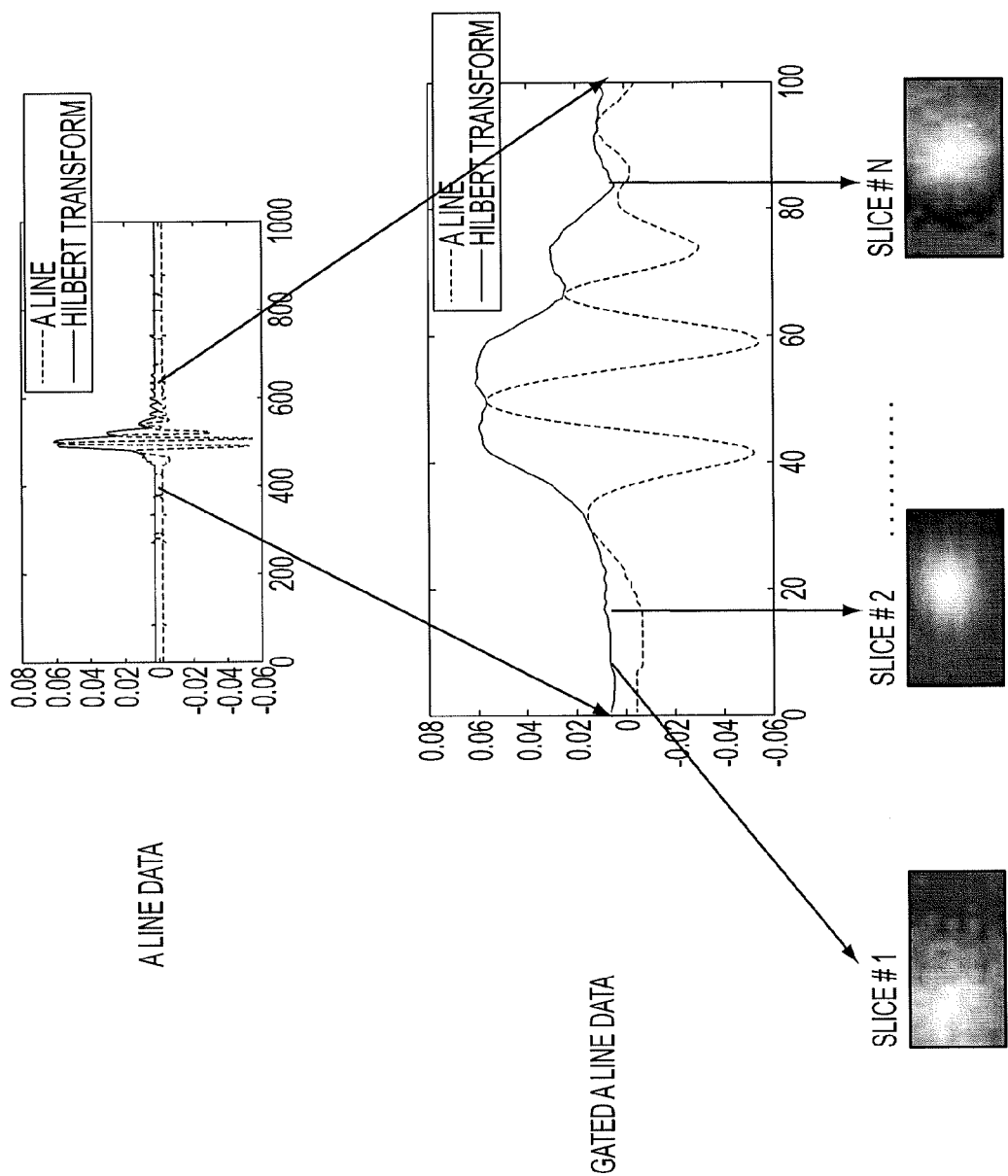
FIG. 5B shows C-scan planar slices of a photoacoustic signal at different time gate centers.
Figure 5C:
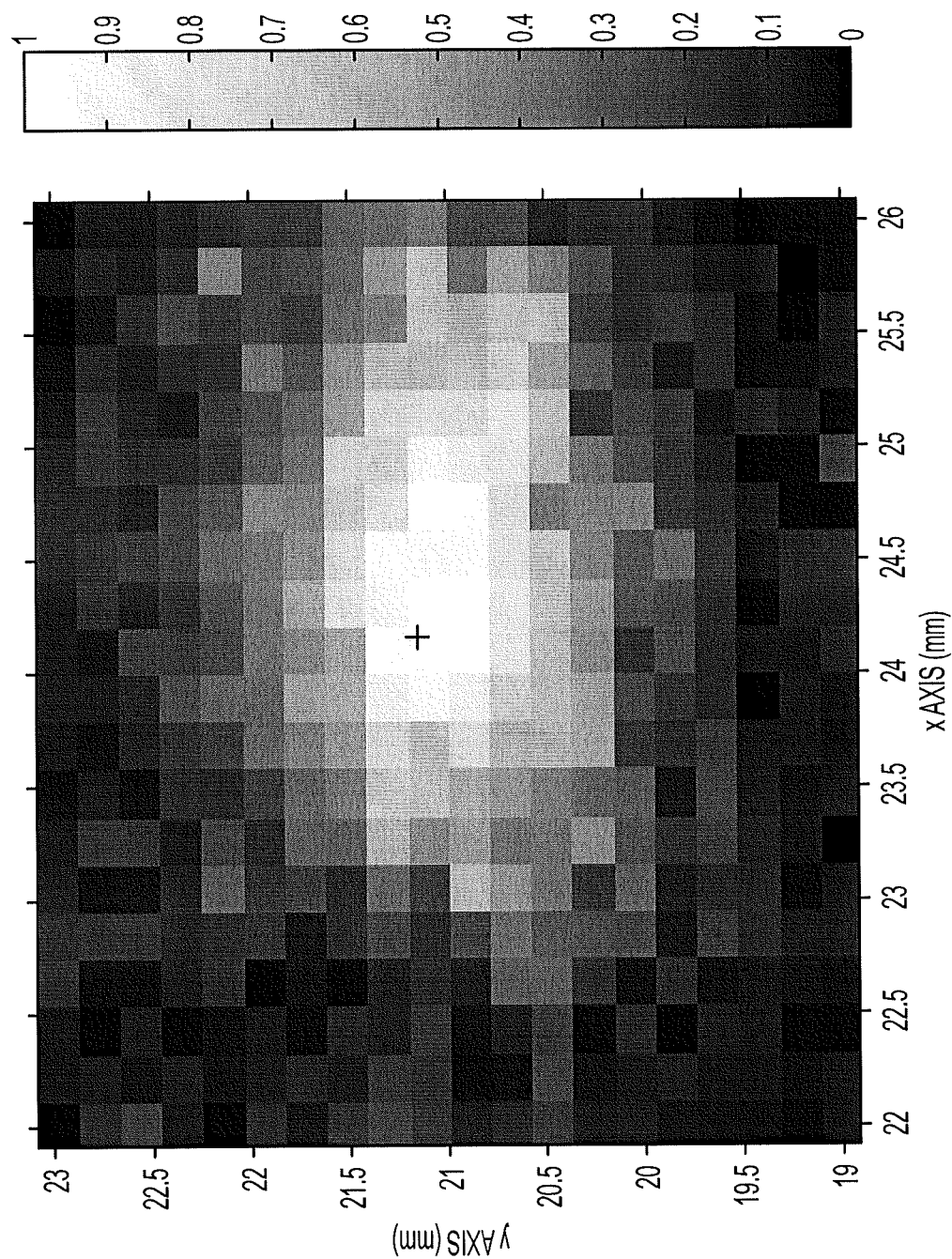
FIG. 5C shows a C-scan image of the lead pencil embedded in chicken breast tissue.

FIG. 5B shows a single PA signal and several time gates chosen for C-Scan. C-Scan planar slices at different time gate centers are also depicted in the figure. FIG. 4 shows the C-Scan image of the point source with fixed OD=55 mm and different ID. This demonstrates that the sharp image is located at an ID of 55 mm corresponding to an OD of 55 mm for a lens of focal length 27.5 mm. FIG. 5C depicts a C-Scan image of the lead pencil embedded in a chicken breast tissue.

Further lens design and fabrication will be performed. In vitro testing of the fabricated lens will be performed using phantoms and prostate gland tissue. Sensing of the PA signal will be done using a 0.1 mm diameter hydrophone. The tip of the hydrophone will be scanned in the image plane point-by-point with a pixel resolution of 100 microns. Lens aberrations, depth of field, in plane spatial resolution and resolution between C-scan planes, including signal to noise ratio are the quality metrics that will be tested. Based on preliminary study it is expected that the in plane and between the C-scan planes resolution of the proposed imaging system will be 250 microns or better.

An important subcomponent of the CSPIP imaging system is the 2D ultrasound sensor array with a 100×100 micron pixel size and a pitch of 100-200 microns. For near real-time processing, there is a need for on-pixel integrated circuit design. No off-the-shelf technology exists at the present time. Currently, complementary metal oxide semiconductor (CMOS) technology appears to be the best platform to work with because it can perform on-pixel processing with action specific integrated circuits (ASIC), is inexpensive to mass produce, consumes less power, and is undergoing rapid developments. This project will look at innovative approaches to chip design where the signal sensing is incorporated into the CMOS process in a way that meets the demands set by the previous stages. Piezoelectric materials such as PZT or PVDF will be laid on top of the CMOS as sensing layer. Sensing of the PA signal at each pixel will take place via the piezoelectric effect that generates charge proportional to the PA signal. CMOS technology with active pixel processing can integrate the charge within a selectable time gate, convert into voltage, and amplify it. The voltage can then be read out pixel by pixel at video rates with existing camera technology. The development work is expected to be centered on the piezoelectric sensor design and its integration into the CMOS technology.

A system according to the invention can integrate a laser source, acoustic lens, and sensor components into a housing assembly that can be used for in vitro and in vivo testing. The laser stimulation module, lens system, and the ultrasound sensor will be housed in a capsule suitable for transrectal insertion to image prostate gland cancer. The capsule will be approximately 1.5×1×1 inches in size. Approximate weight of the capsule when fully assembled will be 12-14 ounces.

Phantoms will be constructed with point and line targets made from high absorption coefficient material such as India ink or anticoagulated animal blood embedded in a low absorption background material. The objective is to map out the point-spread function of the CSPIP system at various points in the 3D space in front of the lens. A secondary objective is to determine the system signal sensitivity and signal-to-noise ratio (SNR). Linearity of the sensor and image contrast will be evaluated. Finally, 3D imaging of the excised prostate gland will be performed before the pathology study to determine the efficacy of PA imaging system to diagnose prostate cancer. An animal model for prostate cancer will be used for testing. Dogs will be injected with canine transmissible venereal sarcoma cell line that produces neoplasm in 15-40 days. TRUS and our prototype PA imaging device CSPIP will be used transrectally for imaging, comparison, and evaluation.

Figure 6:
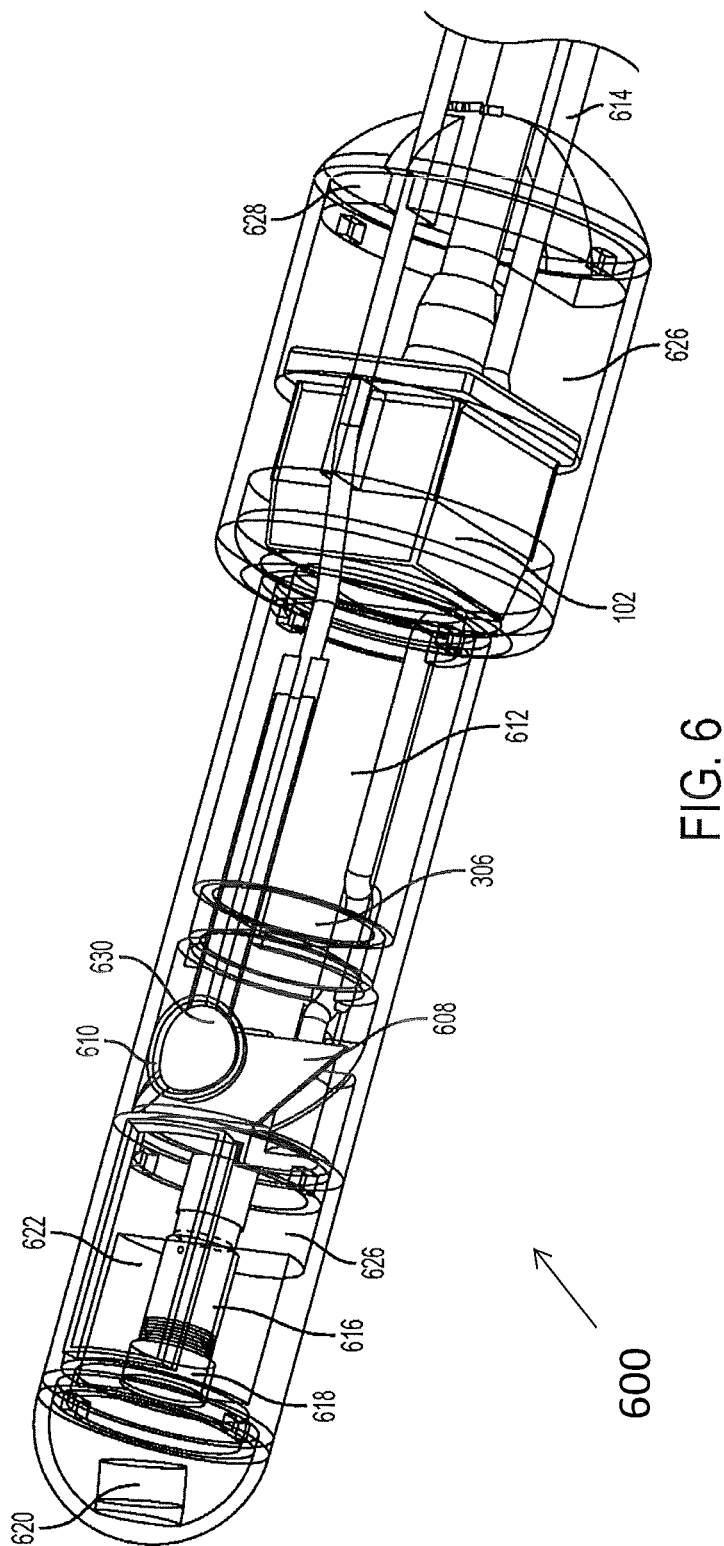
FIG. 6 is a diagram of a probe according to the first preferred embodiment.

A first preferred embodiment of a probe will now be disclosed. The first preferred embodiment, shown in FIG. 6 as 600, is a transrectal prostate probe. Components used for probe construction include: acoustic lens 306, acoustic reflector 608, acoustic window 610, acoustic propagation medium 612, fiber optic cable 614, collimator 616, beam expander 618, optical mirror 620, optical window 622, 2d sensor 102, air 626, probe body 628, and plane wave generator 630. The fiber optic cable is in communication with a laser source (not shown), which can be a photodiode or any other suitable source.

A simple double-concave lens was designed and fabricated to be used as an acoustic lens. The material was chosen as Acrylic whose density is 1.19 g/cm$^3$. The velocity of sound in acrylic medium is 2.75 mm/µs and the acoustic impedance is about 3.26 MRayl. Other excellent candidate materials for acoustic lenses include RTV Silicone rubber (density: 1.49 g/cm$^3$, velocity: 0.92 mm/µs and acoustic impedance: 1.37 MRayl) and agarose hydrogels (velocity of sound: 1.32 mm/µs, acoustic impedance: 1.57 MRayl). The biconcave lens will converge the wavefront from the object plane (tissue) onto the image plane (sensor) with a magnification dictated by the object plane-lens and lens-image plane distances. The lens has a focal length of 27.5 mm and a diameter of 25 mm with a corresponding f number of 1.1. It was designed to produce best images when the object plane-lens distance and the corresponding lens-image plane distance were 55 mm with a resulting magnification of 1.

Stainless steel was used as the acoustic reflector due to its excellent acoustic properties. It has an acoustic impedance of 46 MRayl which is very high compared to that of water. The velocity of sound through stainless steel medium is 5.79 mm/µs. Stainless steel has a density of 7.89 g/cm$^3$. The thickness of the acoustic reflector is 0.254 mm.

Low density polyethylene material was tested and used as acoustic window material. It has an acoustic impedance of 2.12 MRayl and a density of 0.92 g/cm$^3$. Sound travels with a velocity of 1.85 mm/µs through this material. The window has a thickness of is 0.793 mm and accounts for transmission of about 82.8% of the acoustic signals. Other materials that can be used as acoustic window are Hydrogels and TPX (Polymethylpentene). Hydrogels-Agarose gel samples have an acoustic impedance of 1.57 MRayl, very close to that of water. The longitudinal velocity of sound in these materials is about 1.32 mm/µs. Polymethylpentene, commonly called TPX is another excellent material with a transparency of 91% in the visible spectrum and a density of 0.83 g/cm$^3$. The speed of sound in TPX is 2.22 mm/µs.

Water was used as the ultrasonic wave propagation medium. Attenuation of ultrasound in water is 1.65 Np/m and the velocity of sound is 1.497 mm/µs which is close to that of a biological tissue. Water has an acoustic impedance of 1.494 MRayl and a density of 0.998 gm/cm$^3$. Mineral oil can also be used as an alternative for water for this purpose. Water was chosen over mineral oil due to its low attenuation coefficient compared to that of mineral oil which is 2.15 Np/m. The velocity of sound in mineral oil is 1.44 mm/µs. Mineral oil has an acoustic impedance of 1.19 M Rayl and a density of 0.825 g/cm$^3$. Valves 632 for water inlet/outlet were provided in the design that allows for regular maintenance. Any appropriate acoustic propagation medium with acoustic impedance close to 1 M Rayl can be used as appropriate.

This lens technology can also be utilized for focusing reflected ultrasound signal similar to conventional ultrasound imaging. Hence, an input ultrasound source (plane wave generator) was added for ultrasound pulse echo C-scan in addition to PA imaging thus making the device, a dual imaging modality.

The laser source will be a tunable broadband laser with frequencies ranging from 500-1100 nm with a typical pulse width of 10 ns and 1-10 Hz pulse repetition frequency. The laser pulses will be delivered via a high quality fiber optic cable. The laser beam waist at the output of the fiber-optic cable-collimator assembly is typically 2 mm with intensity below 100 millijoules/cm$^2$. Beam divergence will be controlled by an optical lens. This beam will be angled by a laser mirror such that the laser beam comes out from an optical window at grazing angle to the outer surface of the probe.

The probe will have a diameter between 0.75 and 1.25 inches, and a length approximately 5 inches. The acoustic window will be aligned in front of the prostate when inserted into the rectum. With the help of acoustic coupling gel, the PA ultrasound waves generated in the prostate will enter through the acoustic window and guided towards the acoustic reflector. This reflector plate is made from stainless steel which has very high acoustic impedance material compared to water. The acoustic and optical chambers are separate and sealed. The acoustic chamber will contain any appropriate acoustic propagation medium with acoustic impedance close to 1 M Rayl, for example, water, as an acoustic propagation medium. This device will provide the C-scan images corresponding to a tissue thickness less than 1 mm, usually in the range of 700-900 microns over the entire length and width of the prostate by means of the 2d sensor.

A FC-connectorized high power delivery fiber optic cable is used to deliver the pulsed high power laser beam from an external laser source. It features a pure silica core and a bonded hard polymer cladding. The fiber has a numerical aperture of 0.37 which allows for greater light coupling efficiencies. The fiber's core diameter is 600 µm and cladding diameter is 630 µm. The maximum power density that the fiber can withstand is 100 KW/cm$^2$. This fiber is suitable for use in the 500 nm to 1100 nm wavelength range.

An FC-connectorized fiber optic collimator is used to collimate the diverging output laser beam from the fiber. The numerical aperture of the collimator is 0.25, with a full beam divergence of 0.048° and 1/e$^2$ output beam diameter of 2 mm. It has a focal length of 11 mm.

Cylindrical and spherical plano-concave lenses are used as beam expanders depending on the application to diverge the collimated beam. Cylindrical lenses provide four times higher laser exposure on the tissue compared to spherical lenses. The lenses have a focal length of −15 mm which facilitates in illuminating the tissue volume over a width of about 1 cm. The size of the cylindrical lens was 10 mm×12 mm with a clear aperture greater than 90% of surface dimensions. The spherical lens has a diameter of 12.7 mm with a clear aperture greater than 90% of its diameter.

A laser mirror of diameter 12.7 mm and thickness 6 mm is used to reflect the diverging beam resulting from the optical lens onto the tissue. It has a high damage threshold of 5 J/cm$^2$ for a 10 ns pulse. Reflectivity of the mirror is greater than 99.7% with a clear aperture greater than 80% of diameter.

A BK7 ¼ wave laser line window of dimensions 35 mm×15 mm and thickness 3 mm was used as an optical window to allow light propagation onto the tissue.

A two-dimensional PZT sensor array will be designed and fabricated with on-pixel processing capabilities that can provide C-scan images in real time. The frequency bandwidth of the sensor will be 2-15 MHz. The sensor will provide C-scan images with slice thickness in the range of 700 to 900 microns. Behind the sensor, action specific integrated circuits will be employed to read the voltage at each pixel, amplify, convert it from analog to digital format and read out on the display.

The laser light beam is allowed to propagate through air before passing out of the optical window. It also ensures that the sensor's backend electronics are insulated from water (or whatever acoustic propagation medium is used).

The probe body is made of a material called watershed XC11122. Its properties mimic traditional engineering plastics including ABS and PBT. The size of the probe depends mainly on the application. In case of the prostate, it is designed as side-fire probe, and in case of applications like breast, skin, thyroid or transvaginal imaging, it will be designed as end-fire probe or its variables.

A high bandwidth ultrasonic transducer of 5 MHz nominal center frequency is used as a plane wave generator whose electrical impedance will be well matched to conventional ultrasound pulsar/receivers. The transducer will have a low Q-factor (air-backed into PMMA) and conforms perfectly to the probe's cylindrical surface. Typical thickness of this plane wave generator would be 110 microns (dual layer) with a low electrical impedance of 30 to 100 ohms. It will be bonded with epoxy resin or a transfer adhesive to acoustic window material and then be used.

Figure 6A:
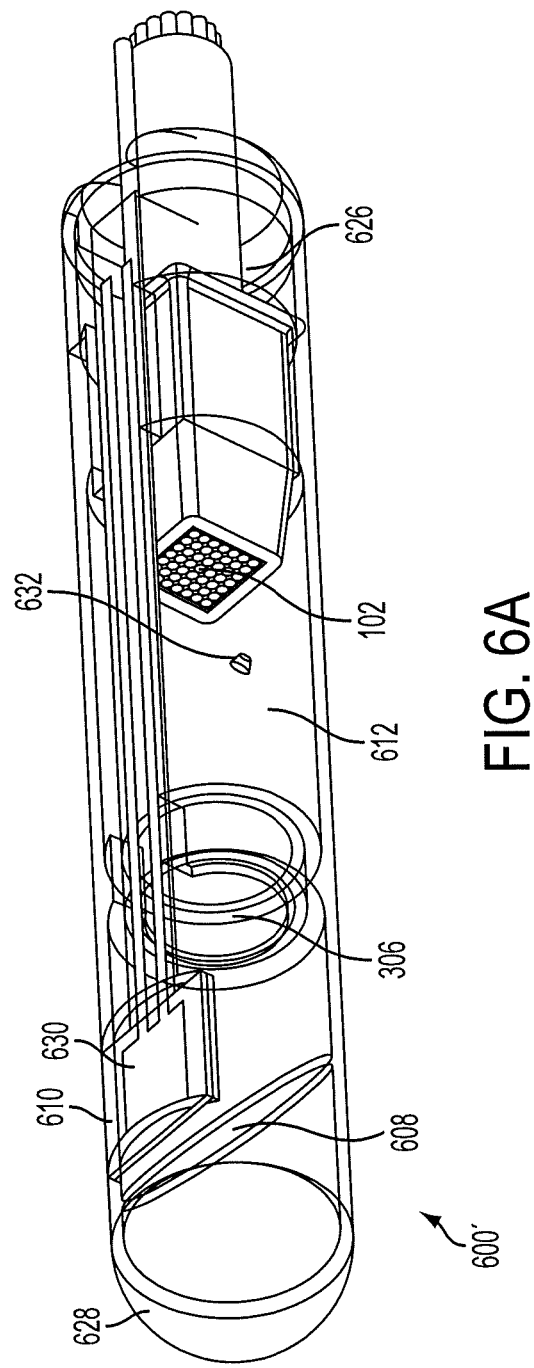
FIGS. 6A and 6B are diagrams of a variation of the probe of FIG. 6
Figure 6B:
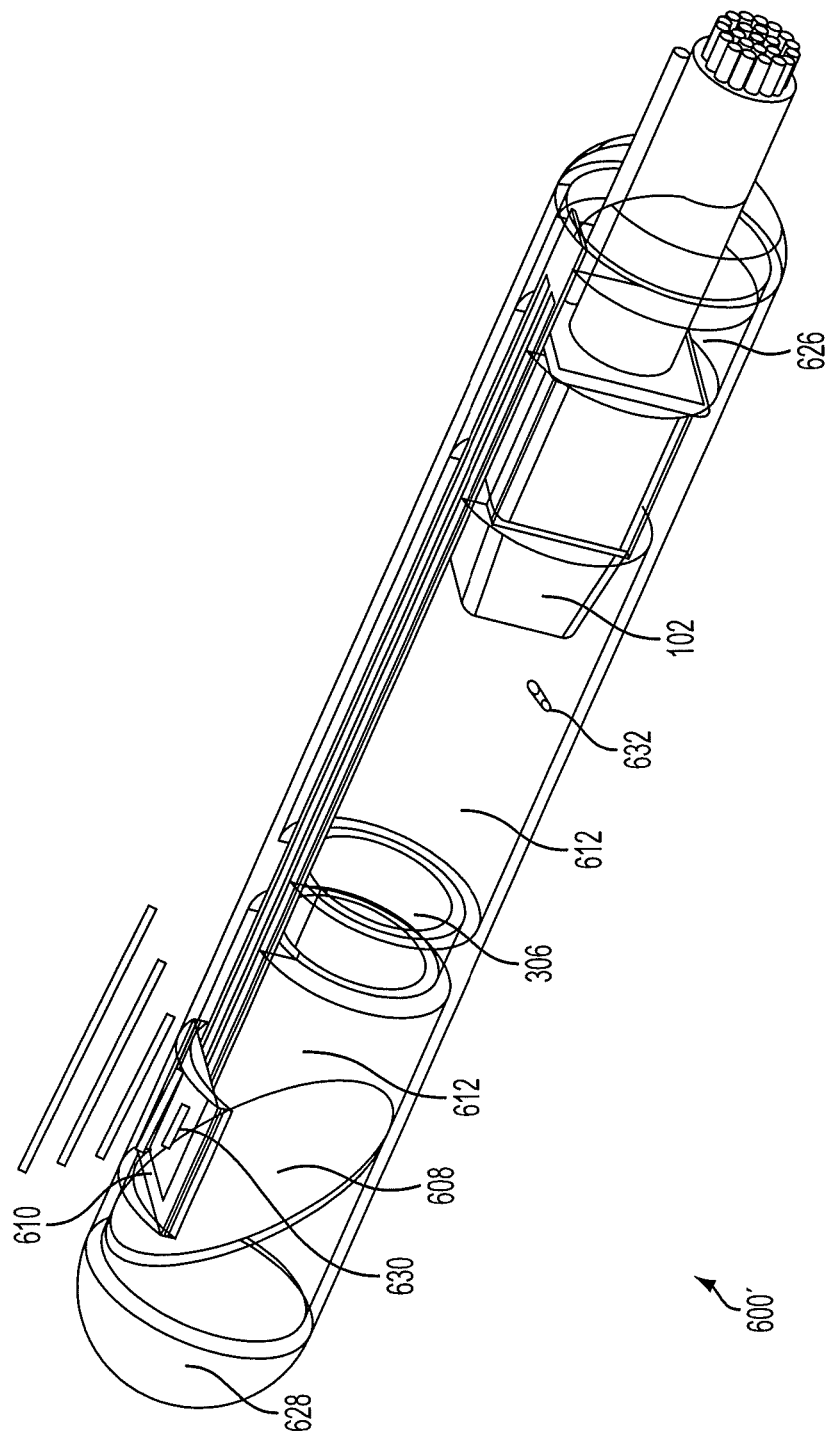

A variation of the first preferred embodiment will be described with reference to FIGS. 6A and 6B. The variation, shown in FIGS. 6A and 6B as 600', uses ultrasound only rather than both ultrasound and the photoacoustic effect and is constructed like the previously described probe 600, except for the omission of elements relating solely to the photoacoustic effect and for any differences described herein. The device 600' will facilitate the definitive detection of prostate cancer and generates C-scan multiplanar images. An input ultrasound source (plane wave generator) was added for ultrasound pulse echo C-scan imaging while focusing of each plane happens in real time with the help of acoustic lens.

The probe will have a diameter between 0.75 and 1 inches, and a length approximately 5 inches. The acoustic window will be aligned in front of the prostate when inserted into the rectum. With the help of acoustic coupling gel, the ultrasound waves reflected from the prostate will enter through the acoustic window and guided towards the acoustic reflector. This reflector plate is made from stainless steel which has very high acoustic impedance material compared to water. Water is used as acoustic propagation medium because of its low ultrasound attenuation coefficient compared to mineral oil. Any appropriate acoustic propagation medium with acoustic impedance close to 1 M Rayl can be used. This device will provide the C-scan multiplanar images of the prostate gland.

Figure 7:
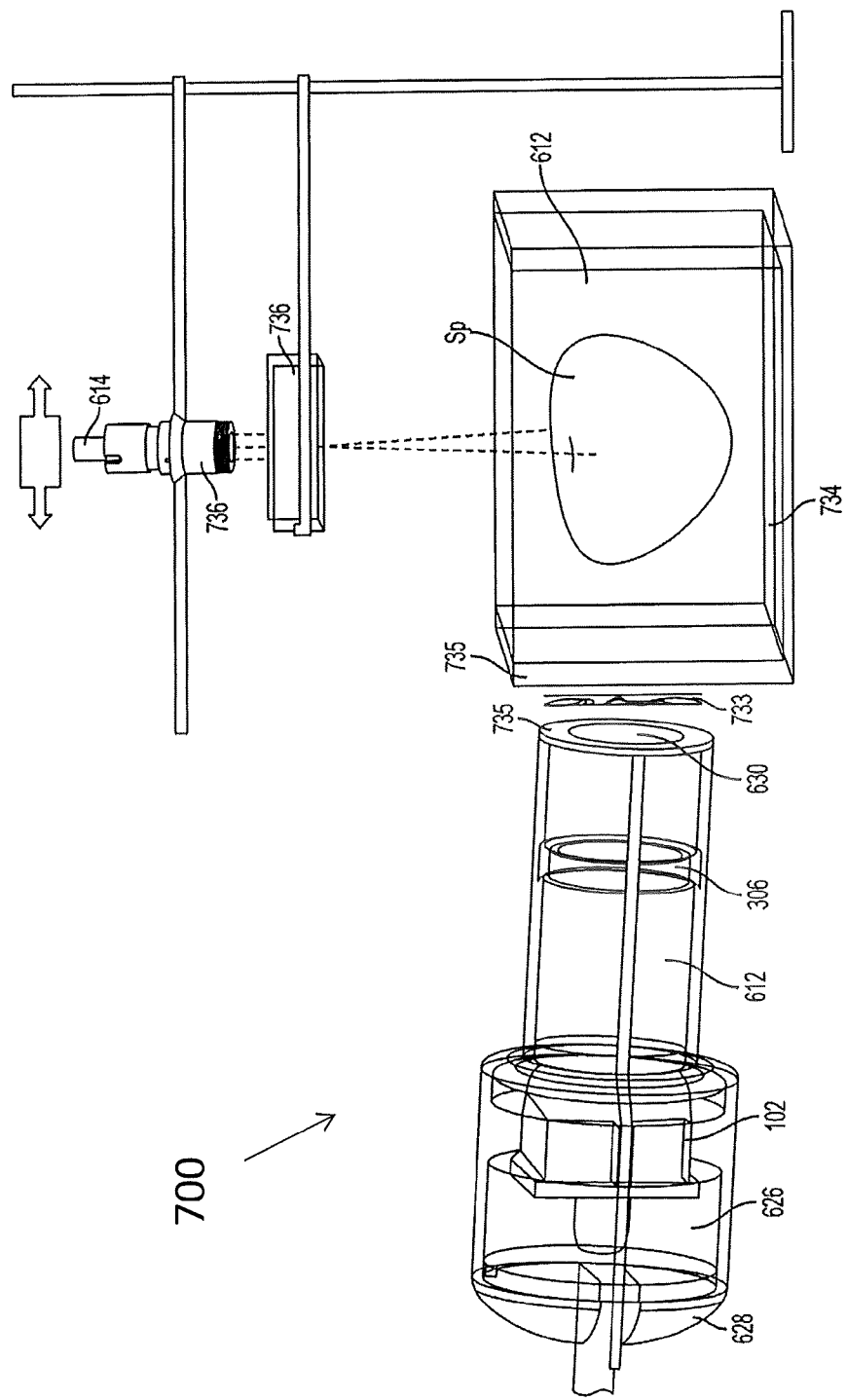
FIG. 7 is a diagram of a system according to the second preferred embodiment.

Another preferred embodiment, shown in FIG. 7 as 700, can be used to evaluate prostate cancer (or cancer of any other organ) in vitro. It is constructed like the first preferred embodiment, except as described below.

When pathologists receive a freshly excised sample with cancer, they are uncertain of the exact location of cancer. In order to determine its location, the specimen will be sliced and visually inspected by naked eye. If any abnormalities are present, the specimens will be examined through histopathology procedure. This device will facilitate the detection of cancer in the tissue for e.g., prostate gland which has been removed by surgery thus aiding the pathologist in locating the cancer. It provides the depth and location of the cancer by calculating all the foci (since the prostate is multifocal) within the prostate gland. This procedure saves a lot of time and will help in appropriate staging of prostate cancer. This device can be used not only for prostate but also for detecting cancer in any other organ of the body such as ovary, testis, uterus, kidney etc. that has been submitted to the pathologist for evaluation. This device will provide the C-scan images corresponding to a tissue thickness less than 1 mm, usually in the range of 700-900 microns over the entire length and width of the prostate.

The specimen Sp is usually setup in a water bath 734 to ensure maximum acoustic matching between the tissue and the medium. Any appropriate acoustic propagation medium with acoustic impedance close to 1 M Rayl can be used instead. The acoustic window will be aligned in front of the prostate during the examination. With the help of acoustic coupling gel 733 and acoustic windows 735, the PA ultrasound waves generated in the prostate will enter through the acoustic window and focused onto the sensor by means of the acoustic lens. Water (or other acoustic propagation medium, as noted) is filled inside the probe which acts as the acoustic propagation medium. Scanning optics 736 allow scanning of the light over the sample.

Figure 8:
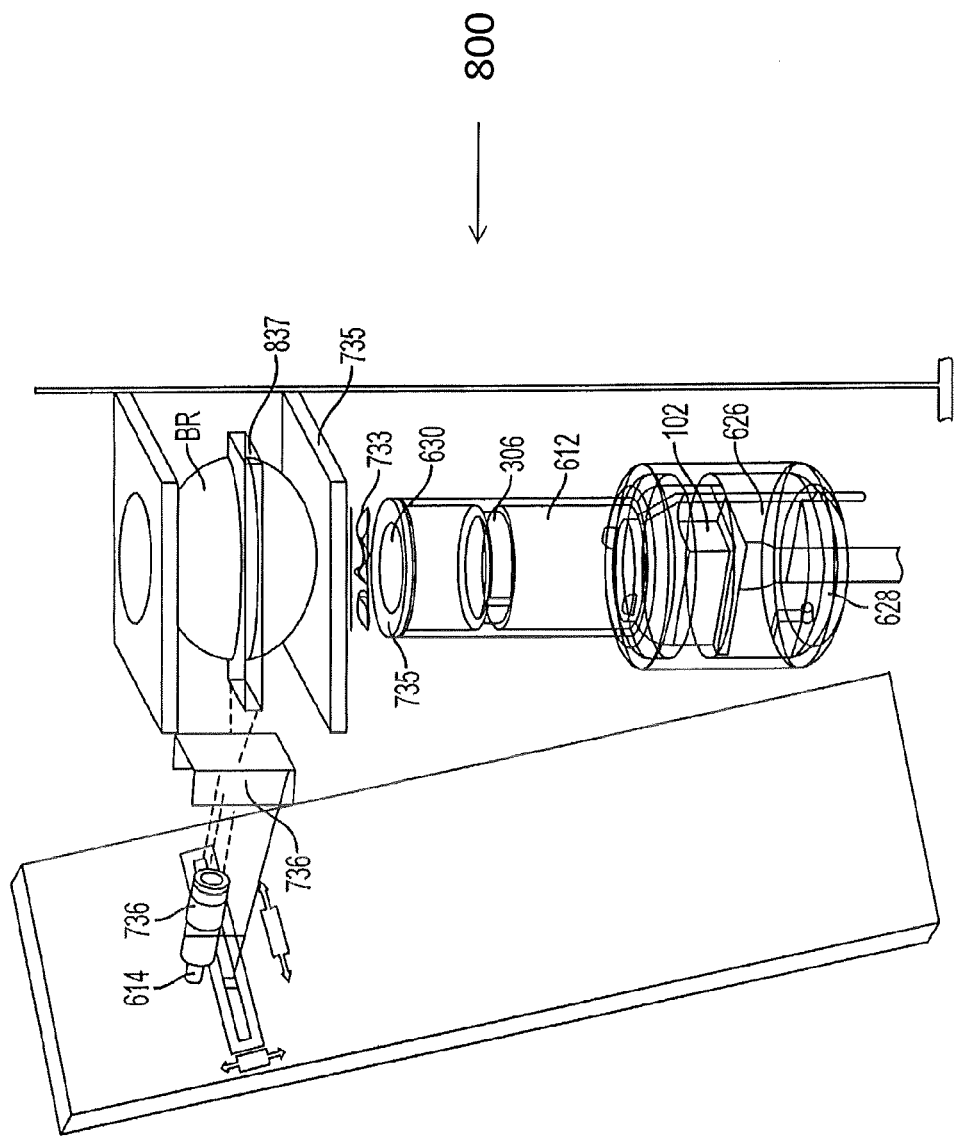
FIG. 8 is a diagram of a system according to the third preferred embodiment.
Figure 8A:
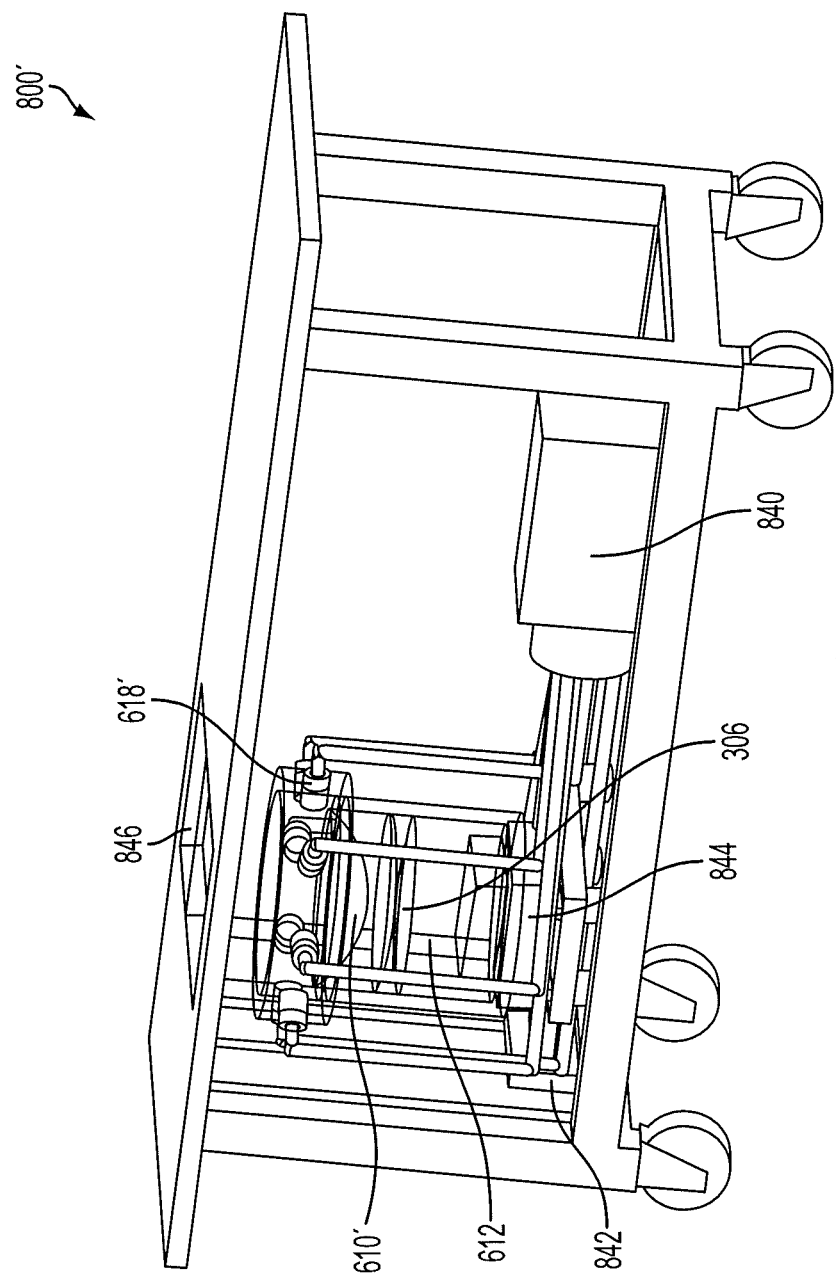
FIGS. 8A-8D are diagrams of a system according to a first variation of the third preferred embodiment.
Figure 8B:
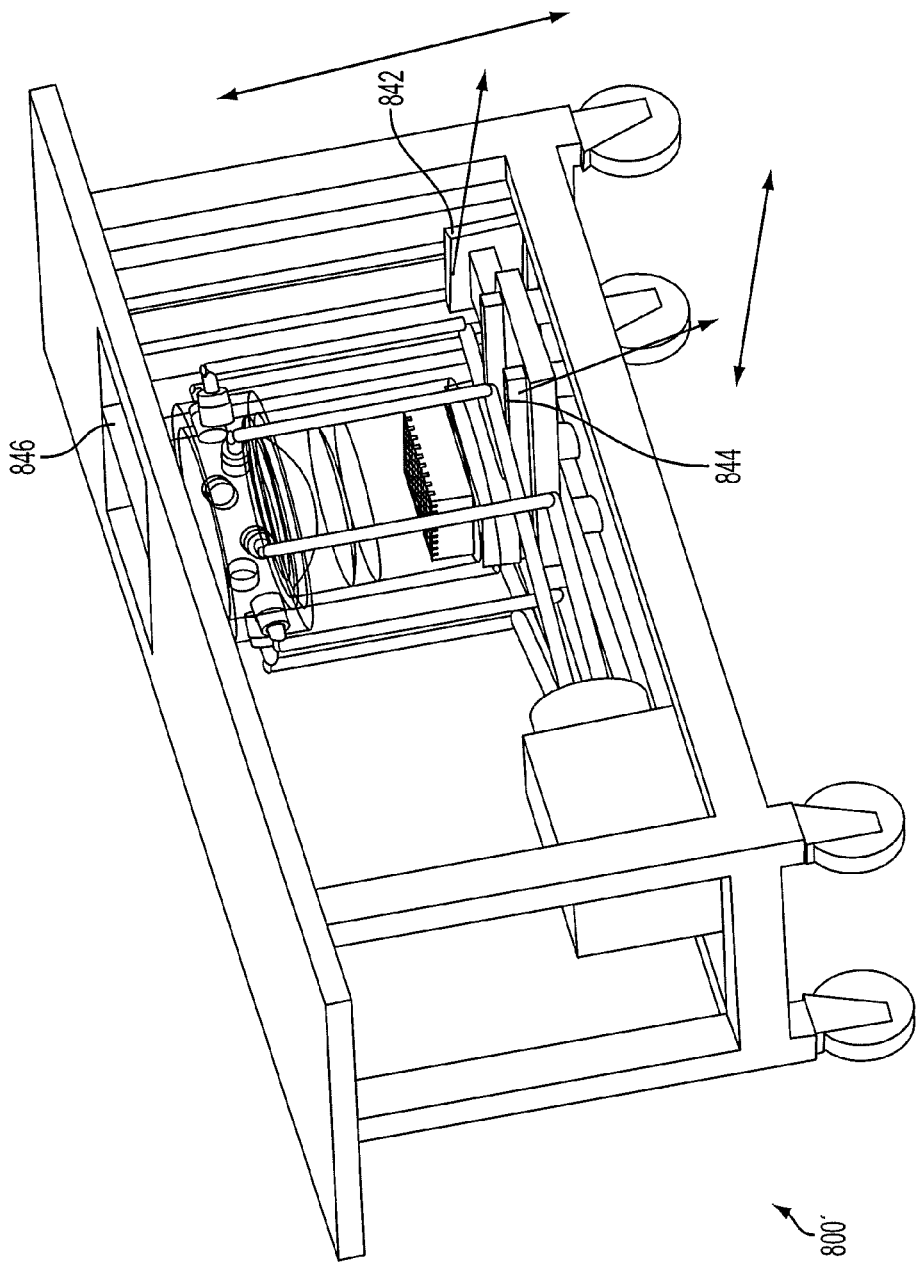
Figure 8C:
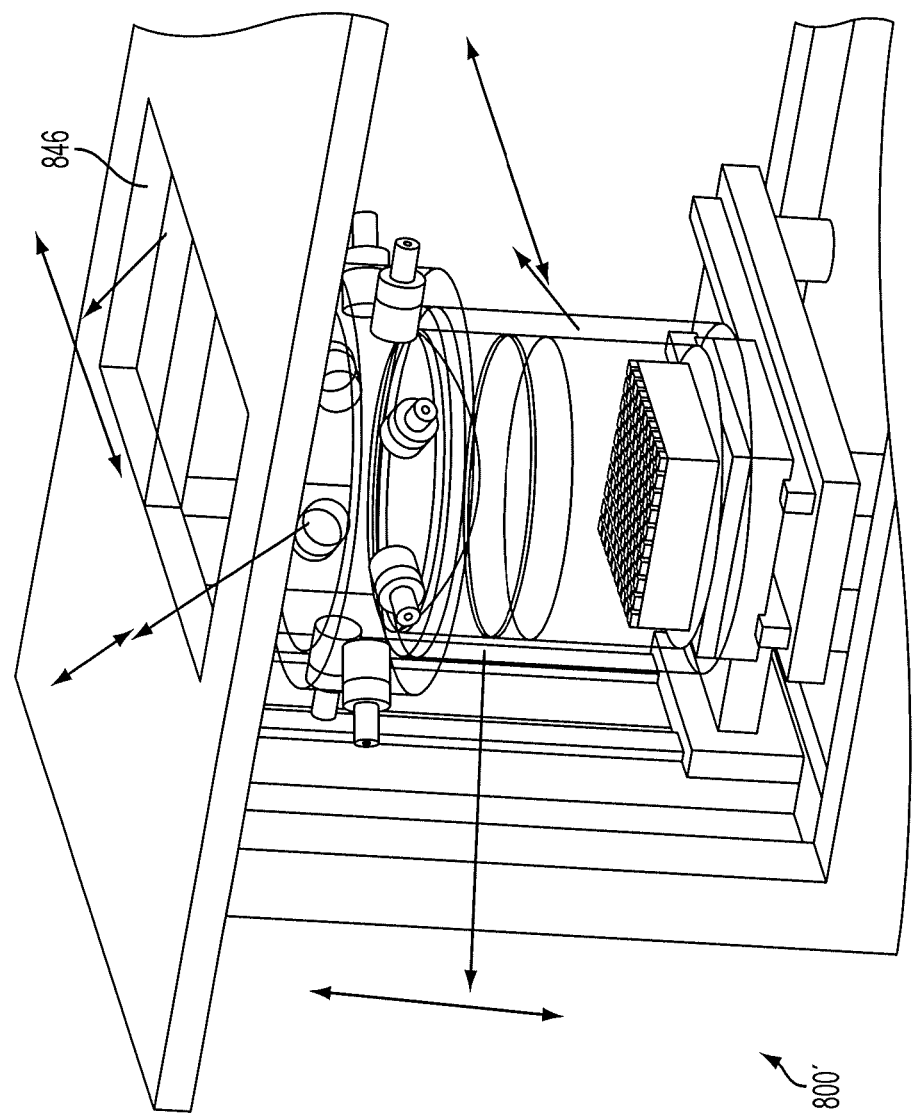
Figure 8D:
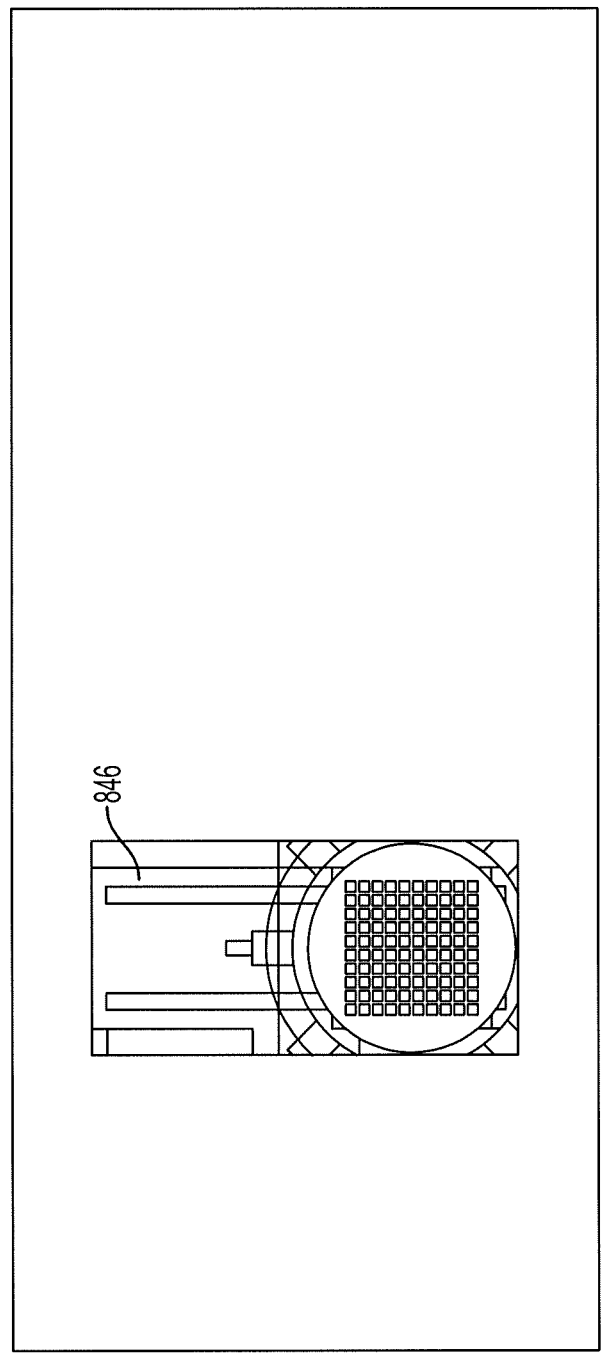

A third preferred embodiment, shown in FIG. 8 as 800, can be used for breast imaging. It is constructed like the first and second preferred embodiments, except as described below.

Breast cancer is the highest incident cancer among the women worldwide. Although the techniques such as x-ray mammography, ultrasound imaging and biopsy are currently used to detect and diagnose breast cancers, they all suffer from drawbacks including high rate of missed positives, use of ionizing radiation and patient discomfort.

The third preferred embodiment generates C-scan planar images, depicting the entire breast in sequential transverse planes. Focusing of each plane happens in real time with the help of the acoustic lens. The lens will be large enough for the photoacoustic signals generated from the entire breast volume to propagate towards the receiver. A breast holder 837 holds the breast Br.

A first variation of the third preferred embodiment is shown in FIGS. 8A-8D as 800'. The first variation uses the photoacoustic effect only and can be constructed like the system 800 according to the third preferred embodiment, except for the omission of the plane wave generator and any changes set forth herein.

The device will facilitate the definitive detection of breast cancer and generates C-scan multiplanar images of the breast. The device includes a table that can be built into a hospital bed. It has a vent (sliding door 846) on the top to allow free hanging of the breast that needs to be imaged. During the examination, only one of the breasts (either left or right) will be compressed with a compression plate and the other one that needs to be imaged will be allowed to protrude through the vent provided. The probe will have a diameter between 3 and 5 inches, and a length approximately 3 inches, and it includes an acoustic window that is curved inwards to ensure matching between the breast surface and the acoustic propagation medium (any appropriate acoustic propagation medium with acoustic impedance close to 1 M Rayl, for example, water) inside the probe. This probe which consists of acoustic lens, water and the sensor will be mounted onto a translation stage that can move horizontally from left to right depending on the side being imaged. Also, this entire stage is provided a vertical translation movement to make sure that the probe is in contact with the breast before the exam is started.

Focusing of each plane happens in real time with the help of the acoustic lens. The lens will be large enough for the photoacoustic signals generated from the entire breast volume to propagate towards the sensor. The laser source will be a tunable broadband laser with frequencies ranging from 500-1100 nm with a typical pulse width of 10 ns and 1-10 Hz pulse repetition frequency. The laser pulses will be delivered via a bundle of high quality fiber optic cables. The laser beam waist at the output of the fiber-optic cable is typically 2 mm with intensity below 100 millijoules/cm$^2$. The fiber-optic cables are arranged in a circular fashion and are equipped into a ring around the breast. The fiber-optic cables are terminated onto compound lens-beam expanders which can move back and forth for controlled illumination of the breast.

The laser beams irradiate the breast from all the directions so that the entire breast will become the source of photoacoustic signals. With the help of acoustic coupling gel, the photoacoustic waves generated in the breast enter through the acoustic window and are focused by the acoustic lens onto the sensor and the C-scan images are generated. Water is used as the acoustic propagation medium. Any appropriate acoustic propagation medium with acoustic impedance close to 1 M Rayl could be used instead. This device will provide the C-scan images corresponding to a tissue thickness less than 1 mm, usually in the range of 700-900 microns over the entire length and width of breast by means of the 2d sensor.

The acoustic lens will converge the wavefront from the object plane (tissue) onto the image plane (sensor) with a magnification dictated by the object plane-lens and lens-image plane distances. It produces best images when the object plane-lens distance and the corresponding lens-image plane distance are at a distance of twice the lens-focal length with a resulting magnification of 1. The lens will be large enough to ensure that the acoustic signals from the entire breast are received by the sensor.

The shape of the acoustic window 610' in this case will follow a concave pattern to ensure maximum acoustic match between the breast and the acoustic propagation medium (any appropriate acoustic propagation medium with acoustic impedance close to 1 M Rayl, for example, water) inside the probe so that the signal-to-noise ratio is maximized.

A group of high power delivery fiber optic cables will be used to deliver the pulsed high power laser beam from an external laser source. They feature a pure silica core and a bonded hard polymer cladding. The fibers have a larger numerical aperture that allows for greater light coupling efficiencies. The fiber's core diameter is typically 600 μm and cladding diameter is 630 μm. The maximum power density that the fiber can withstand is 100 KW/cm$^2$. These fibers will be suitable for use in 500 nm to 1100 nm wavelength range.

Cylindrical and spherical plano-concave lenses will be used as beam expanders 618' to diverge the light beam coming out of the fibers. These lenses will also allow focusing like camera-zoom lenses. Depending on the desired area to be imaged, the area over which the light is irradiated will be controlled with the aid of them. Cylindrical lenses provide four times higher laser exposure on the tissue compared to spherical lenses. The lenses have a focal length of −15 mm which facilitates in illuminating the tissue volume over a width of about 1 cm. The lenses have their clear apertures greater than 90% of surface dimensions.

A high energy broadband tunable pulsed laser source 840 with a typical pulse repetition rate of 10 Hz and pulse duration of 10 ns will be employed as the external laser source to generate laser beam of desired size. The exposure energy will be lower than the maximum permissible exposure limits set by ANSI 136.1 standards for the human tissue. A Ti:Sapphire laser coupled to Nd:YAG laser through a frequency doubler will provide a wide range of wavelengths that are suitable for photoacoustic imaging.

There are two translation stages incorporated in the design. The first one, 842, is for vertical movement of the acoustic lens-sensor configuration along with the circular ring with fiber optic cables to adjust according to the location of the breast. The second one, 844, is for horizontal movement of the detector configuration (along with the lens and the ring with fiber optic cables) to accommodate the left or right breast, which may be accessed through a sliding door 846.

Figure 8E:
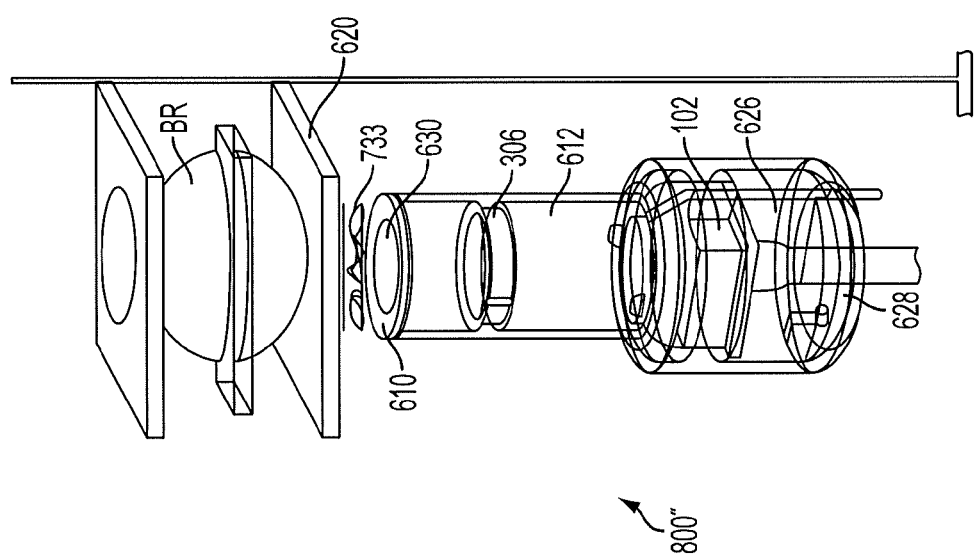
FIG. 8E is a diagram of a system according to a second variation of the third preferred embodiment.

A second variation of the third preferred embodiment, shown in FIG. 8E as 800", is used for breast ultrasound. It can be constructed like the third preferred embodiment 800, except for the omission of the elements concerned only with the photoacoustic effect and for any differences described herein.

The device 800" will facilitate the definitive detection of breast cancer and generates C-scan multiplanar images of the breast. An input ultrasound source (plane wave generator) is used for ultrasound pulse echo C-scan imaging. Focusing of each plane happens in real time with the help of the acoustic lens. The lens will be large enough for focusing the ultrasound signals reflected from the entire breast volume to propagate towards the receiver. The breast is compresses during the examination and the C-scan images over the entire volume of the breast are produced by the device. The probe including the acoustic window, acoustic lens and the 2d sensor is brought in contact with the acoustically transparent compression plate from the bottom.

The probe will have a diameter between 3 and 5 inches, and a length approximately 3 inches. With the help of acoustic coupling gel, when the plane wave generator produces the ultrasound waves, they get reflected form the breast and propagate back through the acoustic window, and will be focused onto the image plane (2d sensor) with the help of an acoustic lens. Water is used as acoustic propagation medium. Any appropriate acoustic propagation medium with acoustic impedance close to 1 M Rayl could be used instead. This device will provide the C-scan images corresponding to a tissue thickness less than 1 mm, usually in the range of 700-900 microns over the entire length and width of breast by means of the 2d sensor.

Figure 9:
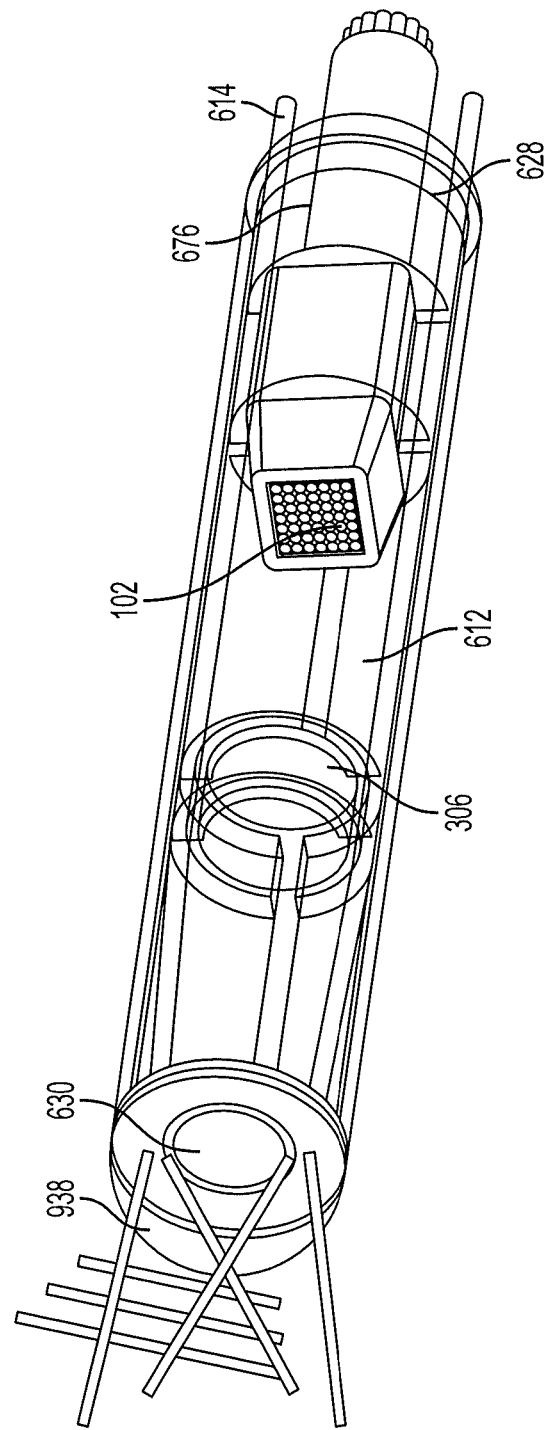
FIG. 9 is a diagram of a system according to the fourth preferred embodiment.
Figure 10:
FIG. 10 is a traditional transrectal sonogram of a prostate with confirmed prostate cancer.

The fourth preferred embodiment, shown in FIG. 9 as 900, is a transvaginal photoacoustic and ultrasound C-scan probe. It is constructed like the first through third preferred embodiments, except as described below.

In the opto-acoustic window 938, an appropriate material will be used that allows both the optical beam and ultrasound waves with minimal transmission losses.

To diagnose the cause of certain types of infertility, pelvic pain, abnormal bleeding, and menstrual problems, transvaginal ultrasound is used. It is often used to show the lining of the uterus. Though the test may reveal certain conditions such as pelvic infection or monitor the growth of the fetus during the pregnancy, it suffers from false positive results in detecting ovarian cysts, ovarian tumors and the cancers of the uterus, vagina and other pelvic structures.

The fourth preferred embodiment generates C-scan planar images, depicting the entire uterus or ovaries in sequential planes. Focusing of each plane happens in real time with the help of the acoustic lens.

The tip of the probe is made optically as well as acoustically transparent with the help of an opto-acoustic window. The delivery of light through two fiber-optic cables ensures that more area is exposed to light thus resulting in the generation of photoacoustic signals from a larger area.

The probe will have a diameter between 0.75 and 1 inches, and a length approximately 5 inches. The opto-acoustic window will be aligned in front of the uterus when inserted into the vagina. With the help of acoustic coupling gel, the PA ultrasound waves generated in the tissue will enter through the acoustic window and focused onto the sensor by means of acoustic lens.

While preferred embodiments have been set forth in detail above, those skilled in the art who have reviewed the present disclosure will readily appreciate that other embodiments can be realized within the scope of the invention. For example, numerical examples are illustrative rather than limiting, as are recitations of specific materials. Also, other embodiments can facilitate in detecting and diagnosing the lesions and tumors associated with lymph nodes, the liver, the gall bladder, the pancreas, the thyroid gland, and the skin. Indeed, the present invention could be adapted for any medical or veterinary imaging or even for non-biological imaging. Moreover, while water has been disclosed as an acoustic propagation medium, any other acoustic propagation medium having appropriate acoustic impedance and other qualities could be used instead. Therefore, the present invention should be construed as limited only by the appended claims.

We claim:

1. A method for imaging a region of interest, the method comprising:
    (a) stimulating the region of interest with light from a light source to produce a set of ultrasound waves through a photoacoustic effect;
    (b) focusing the set of ultrasound waves through an acoustic lens to produce focused waves, the acoustic lens being configured such that said ultrasound waves originating at a single time at an object plane in the region of interest are focused onto an image plane and arrive at the image plane at times separated by no more than a time gate width so that all points in the object plane are focused simultaneously;
    (c) detecting the focused waves in a transducer while applying a time gate corresponding to the time gate width to produce time-gated photoacoustic signals, the time-gated photoacoustic signals providing at least one photoacoustic C-scan at any given period of time, step (c) being repeated multiple times to provide real-time imaging; and
    (d) imaging the region of interest from the at least one photoacoustic C-scan provided in steps step (c).

2. The method of claim 1, wherein, in step (a), the light comprises laser light from a laser light source.

3. The method of claim 2, wherein the laser light is generated by a photodiode.

4. The method of claim 2, wherein the light source comprises an optical fiber in communication with the laser light source.

5. The method of claim 1, wherein, during steps (a) and (b), the light source and the transducer are scanned relative to the region of interest.

6. The method of claim 5, wherein the light source and the transducer are provided in a rigid assembly, and wherein the rigid assembly is scanned during steps (a) and (b).

7. The method of claim 5, wherein the light source and the transducer are scanned in two dimensions.

8. The method of claim 5, wherein the light source and the transducer are scanned in three dimensions.

9. The method of claim 1, wherein the transducer comprises a transducer array.

10. The method of claim 9, wherein the transducer array is a two-dimensional array.

11. The method of claim 1, wherein an optical fiber is used to deliver the light from the light source to the region of interest.

12. The method of claim 1, wherein the region of interest is located in a living body.

13. The method of claim 12, wherein the region of interest is located at least partially in a prostate.

14. The method of claim 12, wherein the region of interest is located at least partially in a breast.

15. The method of claim 12, wherein the region of interest is located at least partially in a pelvic region.

16. The method of claim 15, wherein, during steps (a) and (b), the light source and the transducer are inserted into a vagina.

17. The method of claim 1, wherein the region of interest is located in an in vitro environment.

18. The method of claim 1, wherein step (b) is performed using a single or compound acoustic lens.

19. The method of claim 18, wherein the acoustic lens comprises a biconcave lens.

20. A probe for imaging a region of interest, the probe comprising:
    a light source for stimulating the region of interest with light to produce a set of ultrasound waves through a photoacoustic effect;
    an acoustic lens for focusing the set of ultrasound waves through an acoustic lens to produce focused waves, the acoustic lens being configured such that said ultrasound waves originating at a single time at an object plane in the region of interest are focused onto an image plane and arrive at the image plane at times separated by no more than a time gate width so that all points in the object plane are focused simultaneously; and
    a transducer for detecting the focused waves while applying a time gate corresponding to the time gate width to produce time-gated photoacoustic signals, the time-gated photoacoustic signals providing at least one photoacoustic C-scan at any given period of time, said at least one photoacoustic C-scan being repeated multiple times to provide real-time imaging.

21. The probe of claim 20, further comprising a rigid assembly in which the light source and the transducer are provided.

22. The probe of claim 20, wherein the transducer comprises a transducer array.

23. The probe of claim 22, wherein the transducer array is a two-dimensional array.

24. The probe of claim 20, wherein the light source comprises a laser source.

25. The probe of claim 24, wherein the laser source comprises a photodiode.

26. The probe of claim 24, wherein the light source further comprises an optical fiber.

27. The probe of claim 20, wherein the acoustic lens comprises a single or compound acoustic lens.

28. The probe of claim 27, wherein the acoustic lens comprises a biconcave lens.

29. A method for imaging a region of interest, the method comprising:
- (a) receiving photoacoustic acoustic waves from the region of interest;
- (b) focusing the acoustic waves onto a two-dimensional detector array using an acoustic lens to detect the acoustic waves, the acoustic lens being configured such that said acoustic waves originating at a single time at an object plane in the region of interest are focused onto an image plane and arrive at the image plane at times separated by no more than a time gate width so that all points in the object plane are focused simultaneously; and
- (c) imaging the region of interest in accordance with the acoustic waves detected by the array.

30. The method of claim 29, wherein step (c) comprises time-gating the detected acoustic waves using a time gate corresponding to the time gate width such that a C-scan image is produced.

31. A system for imaging a region of interest, the system comprising:
- a light source for stimulating the region of interest with light to produce ultrasound waves through a photoacoustic effect;
- a two-dimensional detector array;
- an acoustic lens for receiving ultrasound waves from the region of interest and for focusing the ultrasound waves onto the two-dimensional detector array to detect the ultrasound waves, the acoustic lens being configured such that said ultrasound waves originating at a single time at an object plane in the region of interest are focused onto an image plane and arrive at the image plane at times separated by no more than a time gate width so that all points in the object plane are focused simultaneously; and
- a processor, in communication with the array, configured to image the region of interest in accordance with the ultrasound waves detected by the array.

32. The system of claim 31, wherein the processor time-gates the detected acoustic waves using a time gate corresponding to the time gate width such that a C-scan image is produced.

33. A method for imaging a region of interest, the method comprising:
- (a) receiving photoacoustic acoustic waves from the region of interest;
- (b) focusing the acoustic waves using an acoustic lens onto a detector to detect the acoustic waves, the acoustic lens being configured such that said acoustic waves originating at a single time at an object plane in the region of interest are focused onto an image plane and arrive at the image plane at times separated by no more than a time gate width so that all points in the object plane are focused simultaneously;
- (c) time-gating the acoustic waves using a time gate corresponding to the time gate width to produce time-gated acoustic waves; and
- (d) performing a C-scan of the region of interest in accordance with the time-gated acoustic waves.

34. The method of claim 33, wherein the detector comprises a 1D or 2D array.

35. A system for imaging a region of interest, the system comprising:
- a light source for stimulating the region of interest with light to produce ultrasound waves through a photoacoustic effect;
- a detector;
- an acoustic lens for receiving ultrasound waves from the region of interest and for focusing the ultrasound waves onto the detector to detect the ultrasound waves, the acoustic lens being configured such that said ultrasound waves originating at a single time at an object plane in the region of interest are focused onto an image plane and arrive at the image plane at times separated by no more than a time gate width so that all points in the object plane are focused simultaneously; and
- a processor configured for time-gating the ultrasound waves using a time gate corresponding to the time gate width to produce time-gated ultrasound waves and performing a C-scan of the region of interest in accordance with the time-gated ultrasound waves.

36. The system of claim 35, wherein the detector comprises a 1D or 2D array.

37. A method for imaging a region of interest, the method comprising:
- (a) stimulating the region of interest with ultrasound radiation from an ultrasound source to produce a set of ultrasound waves reflected from the region of interest;
- (b) focusing the set of ultrasound waves through an acoustic lens to produce focused waves, the acoustic lens being configured such that said ultrasound waves originating at a single time at an object plane in the region of interest are focused onto an image plane and arrive at the image plane at times separated by no more than a time gate width so that all points in the object plane are focused simultaneously;
- (c) detecting the focused waves in a transducer while applying a time gate to produce time-gated ultrasound signals, the time-gated ultrasound signals providing at least one ultrasound C-scan at any given period of time, step (c) being repeated multiple times to provide said real-time imaging; and
- (d) imaging the region of interest from the at least one ultrasound C-scan provided in step (c).

38. The method of claim 37, wherein the transducer comprises a transducer array.

39. The method of claim 38, wherein the transducer array is a two-dimensional array.

40. The method of claim 37, wherein the region of interest is located in a living body.

41. The method of claim 40, wherein the region of interest is located at least partially in a prostate.

42. The method of claim 40, wherein the region of interest is located at least partially in a breast.

43. The method of claim 40, wherein the region of interest is located at least partially in a pelvic region.

44. The method of claim 37, wherein the region of interest is located in an in vitro environment.

45. The method of claim 37, wherein step (a) is performed using a single or compound acoustic lens.

46. The method of claim 45, wherein the acoustic lens comprises a biconcave lens.

47. The method of claim 37, wherein the ultrasound source comprises a plane wave generator of an acoustic wave.

48. A probe for imaging a region of interest, the probe comprising:
- an ultrasound source for stimulating the region of interest with ultrasound radiation to produce a set of ultrasound waves reflected from the region of interest;

an acoustic lens for focusing the set of ultrasound waves through an acoustic lens to produce focused waves, the acoustic lens being configured such that said ultrasound waves originating at a single time at an object plane in the region of interest are focused onto an image plane and arrive at the image plane at times separated by no more than a time gate width so that all points in the object plane are focused simultaneously; and a transducer for detecting the focused set of waves while applying a time gate to produce time-gated ultrasound signals, the time-gated ultrasound signals providing at least one ultrasound C-scan at any given period of time, said at least one ultrasound C-scan being repeated multiple times to provide said real-time imaging.

49. The probe of claim 48, wherein the transducer comprises a transducer array.

50. The probe of claim 48, wherein the transducer array is a two-dimensional array.

51. The probe of claim 48, wherein the acoustic lens comprises a single or compound acoustic lens.

52. The probe of claim 51, wherein the acoustic lens comprises a biconcave lens.

53. The probe of claim 48, wherein the ultrasound source comprises a plane wave generator of an acoustic wave.

54. A method for imaging a region of interest, the method comprising:
   (a) receiving ultrasound acoustic waves from the region of interest;
   (b) focusing the acoustic waves onto a two-dimensional detector array using an acoustic lens to detect the acoustic waves, the acoustic lens being configured such that said acoustic waves originating at a single time at an object plane in the region of interest are focused onto an image plane and arrive at the image plane at times separated by no more than a time gate width so that all points in the object plane are focused simultaneously; and
   (c) imaging the region of interest in accordance with the acoustic waves detected by the array.

55. A system for imaging a region of interest, the system comprising:
   an ultrasound source for stimulating the region of interest with ultrasound radiation to produce ultrasound waves reflected from the region of interest;
   a two-dimensional detector array;
   an acoustic lens for receiving ultrasound waves from the region of interest and for focusing the ultrasound waves onto the two-dimensional detector array to detect the ultrasound waves, the acoustic lens being configured such that said ultrasound waves originating at a single time at an object plane in the region of interest are focused onto an image plane and arrive at the image plane at times separated by no more than a time gate width so that all points in the object plane are focused simultaneously; and
   a processor, in communication with the array, configured to image the region of interest in accordance with the ultrasound waves detected by the array.

56. A method for imaging a region of interest, the method comprising:
   (a) receiving ultrasound acoustic waves from the region of interest;
   (b) focusing the acoustic waves using an acoustic lens onto a detector to detect the acoustic waves, the acoustic lens being configured such that said acoustic waves originating at a single time at an object plane in the region of interest are focused onto an image plane and arrive at the image plane at times separated by no more than a time gate width so that all points in the object plane are focused simultaneously;
   (c) time-gating the acoustic waves using a time gate corresponding to the time gate width to produce time-gated acoustic waves; and
   (d) performing a C-scan of the region of interest in accordance with the time-gated acoustic waves.

57. A system for imaging a region of interest, the system comprising:
   an ultrasound source for stimulating the region of interest with ultrasound radiation to produce ultrasound waves reflected from the region of interest;
   a detector;
   an acoustic lens for receiving ultrasound waves from the region of interest and for focusing the ultrasound waves onto the detector to detect the ultrasound waves, the acoustic lens being configured such that said ultrasound waves originating at a single time at an object plane in the region of interest are focused onto an image plane and arrive at the image plane at times separated by no more than a time gate width so that all points in the object plane are focused simultaneously; and
   a processor for time-gating the ultrasound waves using a time gate corresponding to the time gate width to produce time-gated ultrasound waves and performing a C-scan of the region of interest in accordance with the time-gated ultrasound waves.

* * * * *